United States Patent
Fredriksson et al.

(10) Patent No.: US 9,677,131 B2
(45) Date of Patent: Jun. 13, 2017

(54) BLOCKING REAGENT AND METHODS FOR THE USE THEREOF

(75) Inventors: Simon Fredriksson, Stockholm (SE); Bonnie Tran, Uppsala (SE)

(73) Assignee: OLINK PROTEOMICS AB, Uppsala (SE)

(*) Notice: Subject to any disclaimer, the term of this patent is extended or adjusted under 35 U.S.C. 154(b) by 841 days.

(21) Appl. No.: 13/809,964

(22) PCT Filed: Jul. 13, 2011

(86) PCT No.: PCT/EP2011/061969
§ 371 (c)(1),
(2), (4) Date: Mar. 25, 2013

(87) PCT Pub. No.: WO2012/007511
PCT Pub. Date: Jan. 19, 2012

(65) Prior Publication Data
US 2013/0171652 A1 Jul. 4, 2013

(30) Foreign Application Priority Data

Jul. 15, 2010 (GB) .................................. 1011971.7

(51) Int. Cl.
*C12Q 1/68* (2006.01)
*G01N 33/542* (2006.01)
*G01N 33/543* (2006.01)

(52) U.S. Cl.
CPC ........... *C12Q 1/686* (2013.01); *C12Q 1/6804* (2013.01); *G01N 33/542* (2013.01); *G01N 33/54393* (2013.01)

(58) Field of Classification Search
None
See application file for complete search history.

(56) References Cited

U.S. PATENT DOCUMENTS

| 5,665,539 A | 9/1997 | Sano et al. |
| 6,511,809 B2 * | 1/2003 | Baez .................... C12Q 1/6804 435/6.11 |
| 7,306,904 B2 | 12/2007 | Landegren |
| 2002/0051986 A1 | 5/2002 | Baez et al. |
| 2011/0318788 A1 * | 12/2011 | Coleman .............. C07D 219/08 435/91.5 |

FOREIGN PATENT DOCUMENTS

| WO | 97/00446 A1 | 1/1997 |
| WO | 01/61037 A1 | 8/2001 |
| WO | 03/044231 A1 | 5/2003 |
| WO | 2004/094456 A2 | 11/2004 |
| WO | 2005/123963 A2 | 12/2005 |
| WO | 2007/044903 A2 | 4/2007 |
| WO | 2007/107743 A1 | 9/2007 |
| WO | 2008/016644 A1 | 2/2008 |
| WO | 2008/122310 A1 | 10/2008 |
| WO | 2009/012220 A2 | 1/2009 |

OTHER PUBLICATIONS

Kang et al. (Bioconjugate Chem 2008, vol. 19, p. 2182-2188).*
Fredriksson et al, Protein detection using proximity-dependent DNA ligation assays. Nat Biotechnol., 20(5):473-7 (2002).
Gullberg et al, Cytokine detection by antibody-based proximity ligation. Proc Natl Acad Sci U S A., 101(22):8420-4 (2004).
Söderberg et al, Characterizing proteins and their interactions in cells and tissues using the in situ proximity ligation assay. Methods, 45(3):227-32 (E pub. Jul. 11, 2008).
Weibrecht et al, Proximity ligation assays: a recent addition to the proteomics toolbox. Expert Rev Proteomics. 7 (3):401-9 (Jun. 2010).
Kang et al, Cellular Delivery and Biological Activity of Antisense Oligonucleotides Conjugated to a Targeted Protein Carrier, Bioconjugate Chem., 19:2182-2188 (2008).

* cited by examiner

*Primary Examiner* — Stephanie K Mummert
(74) *Attorney, Agent, or Firm* — Porter Wright Morris & Arthur LLP

(57) ABSTRACT

The present invention relates to the use of a conjugate of a non-analyte-specific binding protein coupled to a nucleic acid as a blocking reagent in a probe-based detection assay, which uses a probe comprising a proteinaceous analyte-binding partner coupled to a nucleic acid domain to detect an analyte in a sample.

40 Claims, 4 Drawing Sheets

A

B

BLOCKING REAGENT AND METHODS FOR THE USE THEREOF

Figure 1:
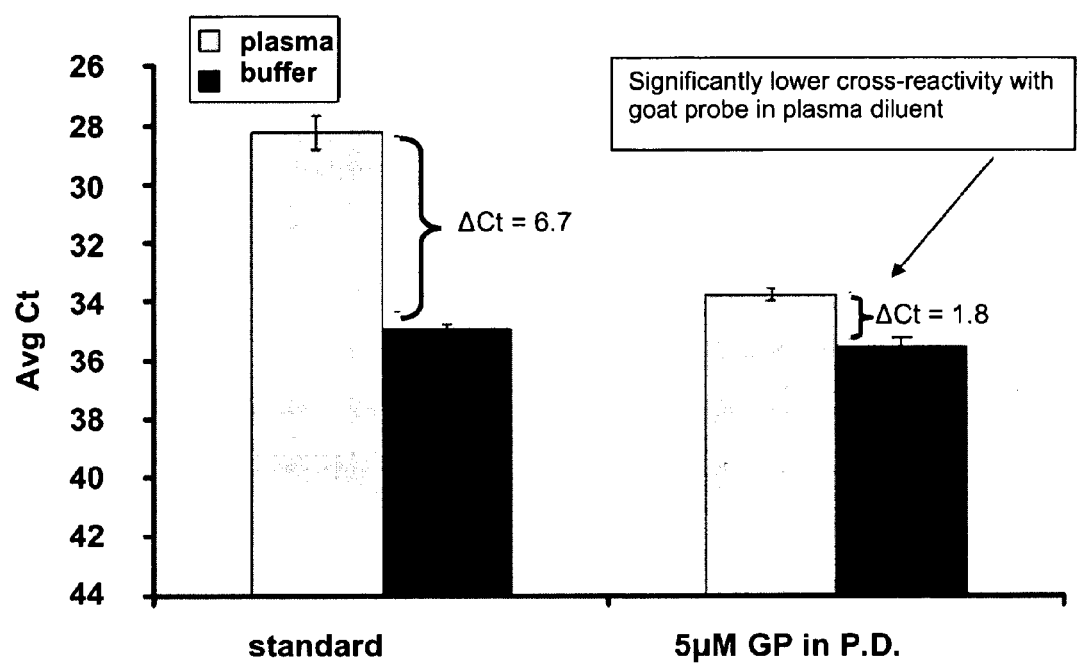

The present invention relates to a proximity-probe based detection assay ("proximity assay") for an analyte in a sample and in particular to an improvement in the method to reduce non-specific "background" signals which arise in complex biological samples. The improvement comprises the provision of a new blocking reagent for use in such assays. The blocking reagent is designed closely to resemble ("mimic") the structure of the proximity probes. The blocking reagent is added to a sample in excess to occupy all or nearly all of the binding sites in the sample capable of non-specifically binding the proximity probe. Thus, in the present invention the observable effect of the blocking reagent is to achieve the equivalent of a reduction in the complexity of the sample without significantly reducing the concentration or amount of analyte present in the sample, thereby increasing both the specificity and sensitivity of the assay. The present invention also provides a blocking reagent, a kit comprising said blocking reagent and a method for producing said blocking reagent.

A proximity assay relies on the principle of "proximity probing", wherein an analyte is detected by the binding of multiple (i.e. two or more, generally two or three) probes, which when brought into proximity by binding to the analyte (hence "proximity probes") allow a signal to be generated. Typically, at least one of the proximity probes comprises a nucleic acid domain (or moiety) linked to the analyte-binding domain (or moiety) of the probe, and generation of the signal involves an interaction between the nucleic acid moieties and/or a further functional moiety which is carried by the other probe(s). Thus signal generation is dependent on an interaction between the probes (more particularly by the nucleic acid or other functional moieties/domains carried by them) and hence only occurs when both the necessary (or more) probes have bound to the analyte, thereby lending improved specificity to the detection system. The concept of proximity probing has been developed in recent years and many assays based on this principle are now well known in the art. For example, proximity ligation assays (PLAs) rely on proximal binding of proximity probes to an analyte to generate a signal from a ligation reaction involving or mediated by (e.g. between and/or templated by) the nucleic acid domains of the proximity assays.

Thus, in a proximity assay proximity probes may be used, which bind to the analyte and have nucleic acid domains, or moieties, which interact in a proximity-dependent manner upon said analyte binding, generally via ligation, to form a detectable, preferably amplifiable, nucleic acid detection product by means of which said analyte may be detected.

Proximity-probe based detection assays, and particularly proximity ligation assays permit the sensitive, rapid and convenient detection or quantification of one or more analytes in a sample by converting the presence of such an analyte into a readily detectable or quantifiable nucleic acid-based signal, and can be performed in homogeneous or heterogeneous formats.

Proximity probes of the art are generally used in pairs, and individually consist of an analyte-binding domain with specificity to the target analyte, and a functional domain, e.g. a nucleic acid domain coupled thereto. The analyte-binding domain can be for example a nucleic acid "aptamer" (Fredriksson et al (2002) Nat Biotech 20:473-477) or can be proteinaceous, such as a monoclonal or polyclonal antibody (Gullberg et al (2004) Proc Natl Acad Sci USA 101:8420-8424). The respective analyte-binding domains of each proximity probe pair may have specificity for different binding sites on the analyte, which analyte may consist of a single molecule or a complex of interacting molecules, or may have identical specificities, for example in the event that the target analyte exists as a multimer. When a proximity probe pair come into close proximity with each other, which will primarily occur when both are bound to their respective sites on the same analyte molecule, the functional domains (e.g. nucleic acid domains) are able to interact, for example, nucleic acid domains may be joined to form a new nucleic acid sequence generally by means of a ligation reaction, which may be templated by a splint oligonucleotide added to the reaction, said splint oligonucleotide containing regions of complementarity for the ends of the respective nucleic acid domains of the proximity probe pair. The new nucleic acid sequence thereby generated serves to report the presence or amount of analyte in a sample, and can be qualitatively or quantitatively detected, for example by realtime, quantitative PCR (q-PCR).

Alternatively, rather than being ligated to each other, the nucleic acid domains of the proximity probes when in proximity may template the ligation of one or more added oligonucleotides to each other, including an intramolecular ligation to circularise an added linear oligonucleotide, for example based on the so-called padlock probe principle, wherein analogously to a padlock probe, the ends of the added linear oligonucleotide are brought into juxtaposition for ligation by hybridising to a template, here a nucleic acid domain of the proximity probe (in the case of a padlock probe the target nucleic acid for the probe). Various such assay formats are described in WO 01/61037.

WO 97/00446 and U.S. Pat. No. 6,511,809 disclose a heterogeneous format for proximity ligation assays, i.e. the analyte is first immobilised to a solid substrate by means of a specific analyte-binding reagent.

Homogeneous proximity ligation assays (i.e., in solution) are disclosed in WO 01/61037, WO 03/044231, WO 2005/123963, Fredriksson et al (2002) Nat Biotech 20:473-477 and Gullberg et al (2004) Proc Natl Acad Sci USA 101: 8420-8424.

Although pairs of proximity probes are generally used, modifications of the proximity-probe detection assay have been described, in e.g. WO 01/61037 and WO 2005/123963, where three proximity probes are used to detect a single analyte molecule, the nucleic acid domain of the third probe possessing two free ends which can be joined (ligated) to the respective free ends of the nucleic acid domains of the first and second probes, such that it becomes sandwiched between them. In this embodiment, two species of splint oligonucleotide are required to template ligation of each of the first and second probes' nucleic acid domains to that of the third.

In a further modification described in WO 2007/107743 the splint oligonucleotide to template ligation of the nucleic acid domains of two proximity probes is carried on a third proximity probe.

Not all proximity assays are based on ligation. WO 2007/044903 discloses proximity probe-based assays for detecting analytes which rely on the formation and detection of a released nucleic acid cleavage product. Some of the described embodiments involve a probe comprised of an analyte-binding moiety and an attached enzyme, which enzyme acts on a nucleic acid moiety attached to the analyte-binding moiety of a second probe, resulting in the release of a detectable nucleic acid cleavage product.

Analyte detection assays, including in some embodiments proximity probe-like reagents, wherein a polymerase enzyme attached to an analyte-binding moiety of one probe acts on a nucleic acid moiety attached to the analyte-binding moiety of a second probe, are described in WO 2009/012220. In these assays, the action of the "tethered" polymerase which is part of one of the probes of a probe pair results in the generation of a template, free in solution, which is susceptible to amplification by an added polymerase. Unlike the tethered polymerase, the added polymerase is only able to act on the template generated by the tethered polymerase, and not directly on the nucleic acid moiety of the non-polymerase-containing probe of the probe pair. The action of the added polymerase results in amplification of the generated template, the amplified copies being detectable and indicative of the presence of analyte in the sample, according to the proximity probing principle.

In addition to modification of the proximity-probe detection assay, modifications of the structure of the proximity probes themselves have been described, in e.g. WO 03/044231, where multivalent proximity probes are used. Such multivalent proximity probes comprise at least two, but as many as 100, analyte-binding domains conjugated to at least one, and preferably more than one, nucleic acid(s).

Proximity-probe based detection assays and particularly proximity ligation assays, have proved very useful in the specific and sensitive detection of proteins in a number of different applications, e.g. the detection of weakly expressed or low abundance proteins. However, such assays are not without their problems and room for improvement exists, with respect to both the sensitivity and specificity of the assay.

The sensitivity of the conventional proximity assays, e.g. proximity ligation assays, as described above, is limited by two main factors: (i) the affinity of the analyte-binding domains for the target analyte and (ii) the non-specific background signal arising from the random proximity of non-bound probes, particularly probe pairs. Using probes having binding domains with high affinity for the analyte, sensitivity is limited to the detection of approximately 6000 molecules. Traditionally, in order to achieve a low level of background, very low concentrations of proximity probes must be used. This precludes any attempt to compensate for probes comprising low affinity analyte-binding domains by using higher concentrations of probe. It has therefore been found that this may limit the sensitivity of the assay, and the range over which quantitative results may be obtained.

Other methods for reducing non-specific background signal have been proposed, such as coupling the splint oligonucleotide to a third proximity probe and/or using blocking oligonucleotides, which bind to the free ends of the nucleic acid domains on the proximity probes until displaced by a splint oligonucleotide. Displacement readily occurs only when the proximity probes are bound to the target analyte (WO 2007/107743). Further methods for reducing background signal have centred on the improving the detection of the ligated nucleic acid.

However, there is still room to improve the level of background signal and in order to overcome the limitations of the proximity assay, particularly proximity ligation assays, known in the art, as described above, it has now been found that the use of a blocking reagent that resembles the structure of the proximity probes, significantly improves the sensitivity and specificity of the assay. Preferably the blocking reagent of the invention is contacted with the sample prior to the addition of the proximity probes. By occupying some or all of the sites in a sample that are capable of non-specifically binding to the proximity probes, the analyte or other components used in the assay it is possible to reduce the non-specific background signal present in the assay.

Whilst the use of reagents to occupy non-specific binding sites is well known in methods used for detecting an analyte in a sample, the nature of the blocking reagent in the present invention provides a unique and unexpected advantage over previously described blocking reagents.

In general, blocking reagents are selected on the basis of being relatively inert and stable molecules that will not interfere with the detection mechanism of the assay in question, but that will bind non-specifically and uniformly to sites within the assay sample that may otherwise bind the analyte or probe. Standard blocking reagents, such as those used in immunoassays, range from abundant and common proteins, e.g. BSA, milk powder, casein, gelatin, and neutral detergents, e.g. CHAPS, Triton X-100, Tween-20 to neutral polymers, e.g. polyvinyl alcohol. In assays involving nucleic acids it is common to block non-specific binding sites with fragmented nucleic acids, e.g. sonicated salmon sperm DNA, poly-A RNA. Furthermore, in is known that combinations of these molecules may be used to reduce the non-specific background signal in an assay.

The blocking reagent of the present invention, however, relies on the superior blocking effect seen when the blocking protein is conjugated or coupled to a nucleic acid. In particular the protein component of the blocking reagent is a protein with very low or preferably no specific binding affinity for the analyte, i.e. a non-analyte-specific binding protein or a non-analyte-specific protein. In a preferred aspect of the invention the protein component of the blocking reagent is selected to mimic or resemble a proteinaceous analyte-binding domain of a proximity probe. Alternatively or additionally, the blocking protein may resemble another protein or proteinaceous moiety which is present in the proximity probe, for example streptavidin or a similar protein which is used in the proximity probe to effect binding of the analyte-binding domain of the probe to the nucleic acid domain. Thus it can be seen that the blocking reagent is a protein-nucleic acid conjugate, and in this way it mimics, or resembles, a proximity probe, which is itself a conjugate of a protein (or proteinaceous molecule) (e.g. the analyte-binding domain) and a nucleic acid. It is the coupling of these two reagents that results in an improved reduction in non-specific background signal in a proximity-probe based assay. As shown in more detail in the Examples, the present invention represents a significant advance over the use of other blocking reagents known in the art. In particular, it is shown that the use of the non-analyte-specific binding protein component of the blocking reagent or the nucleic acid component of the blocking reagent individually are ineffective in reducing the non-specific background signal in proximity-probe based detection assays. Surprisingly, only when the non-analyte-specific binding protein component and nucleic acid component are used in combination in a conjugated form is a dramatic improvement in the blocking effect observed. The use of the individual unconjugated components in combination does not replicate the effect of the conjugated blocking reagent. Thus, it is the conjugation of these two components to form a single blocking reagent that results in a significant and completely unexpected reduction in the non-specific background signal. Furthermore the blocking reagent of the present invention is superior to previously used blocking reagents used in proximity probe based detection assays. The consequence of such a reduction in background signal is an increase in both the specificity and sensitivity of the proximity-probe detection assays. Moreover, the blocking reagent of the invention may be used in combination with other steps to further reduce non-specific background signals.

Accordingly, the invention can be seen to provide the use of a conjugate of a non-analyte-specific binding protein coupled to a nucleic acid as a blocking reagent in a proximity probe-based detection assay which uses a proximity probe comprising a proteinaceous analyte-binding partner coupled to a nucleic acid domain to detect an analyte in a sample.

Alternatively viewed, this aspect of the invention provides a method of detecting an analyte in a sample, which method comprises the use of a proximity probe comprising a proteinaceous analyte-binding partner coupled to a nucleic acid domain, wherein a conjugate of a non-analyte-specific binding protein coupled to a nucleic acid is used as a blocking reagent.

Viewed from yet another aspect, the invention provides a method of reducing non-specific binding of a proximity probe comprising a proteinaceous analyte-binding partner coupled to a nucleic acid domain in a proximity probe-based detection assay for an analyte in a sample, said method comprising adding to said sample a blocking reagent comprising a conjugate of a non-analyte-specific binding protein coupled to a nucleic acid.

However, the use of the blocking reagent of the invention need not be limited only to methods using proximity probes. In view of the favourable results obtained in proximity probe assays (see the Examples) it is envisaged that the blocking reagent would work equally well in any assay which uses a similar probe (i.e. comprising a proteinaceous analyte-binding domain and a nucleic acid domain) including as a single reagent, e.g. immunoassays such as immuno-PCR and immuno-RCA.

Accordingly, at its broadest, the invention can be seen to provide the use of a conjugate of a non-analyte-specific binding protein coupled to a nucleic acid as a blocking reagent in a probe-based detection assay which uses a probe comprising a proteinaceous analyte-binding partner coupled to a nucleic acid domain to detect an analyte in a sample.

Alternatively viewed, this aspect of the invention provides a method of detecting an analyte in a sample, which method comprises the use of a probe comprising a proteinaceous analyte-binding partner coupled to a nucleic acid domain, wherein a conjugate of a non-analyte-specific binding protein coupled to a nucleic acid is used as a blocking reagent.

Viewed from yet another aspect, the invention provides a method of reducing non-specific binding of a probe comprising a proteinaceous analyte-binding partner coupled to a nucleic acid domain in a probe-based detection assay for an analyte in a sample, said method comprising adding to said sample a blocking reagent comprising a conjugate of a non-analyte-specific binding protein coupled to a nucleic acid.

In one aspect of the invention, the method of the invention is, and the blocking reagent is for use in, an immunoassay, preferably wherein said immunoassay is an immuno-PCR. The immunoassay may be any of the assays known in the art that utilise a probe comprising a proteinaceous analyte-binding partner coupled to a nucleic acid domain for the detection of an analyte. The blocking reagent of the invention may be particularly useful in immuno-PCR assays, e.g. as described in U.S. Pat. No. 5,665,539, which use a single probe, as hereinbefore defined, to detect an analyte which has been immobilised. The probe is captured onto the solid phase via its interaction with the analyte and the nucleic acid domain of the probe can be detected by an amplification reaction.

In an alternative aspect of the invention the method of the invention is, and the blocking reagent is for use in, a proximity-probe based assay and the probe is a proximity probe. The proximity probe-based detection assay (proximity assay) may be any of the assays known in the art, for example as described above, which use proximity probes to detect an analyte in a sample. Advantageously, the invention may be used in the context of assays in which at least two (or all) the proximity probes in the assay are based on protein-nucleic acid conjugates (i.e. comprise a proteinaceous analyte-binding domain coupled to a nucleic acid domain). Notably, such an assay will be a proximity ligation assay, although the invention is not limited to detecting interactions between the nucleic acid domains of proximity probes based on ligation (for example the interaction between the nucleic acid domains may be based on hybridisation or hybridisation and extension, as disclosed for example in WO 97/00446 or WO 01/61037).

Accordingly, in one preferred aspect the present invention provides a method for detecting an analyte in a sample, comprising:

(a) contacting said sample with a blocking reagent comprising a non-analyte-specific binding protein coupled to a nucleic acid;

(b) further contacting said sample with at least one set of at least first and second proximity probes, which probes each comprise a proteinaceous analyte-binding domain and a nucleic acid domain and can simultaneously bind to the analyte;

(c) allowing the nucleic acid domains of the proximity probes to interact with each other upon binding of said proximity probes to said analyte, wherein said interaction comprises a ligation reaction; and (d) detecting said ligation.

Whilst not wishing to be bound by theory, it is believed that the method of the invention relies upon the blocking reagent occupying sites within the sample that would otherwise bind to the probes or other components of the assay, thereby interfering with the detection of the analyte.

Thus the blocking reagent of, and for use in the method of, the invention is typically used in an excess, preferably a molar excess, over the respective probes, e.g. an excess of 2-100000 fold, e.g. 20-50000, 50-30000, 100-50000, 100-30000, 1000-20000, 5000-10000 fold e.g., 5, 10, 100, 200, 500, 1500, 3000, 6000 or 12500 fold.

The detection itself depends upon the presence of an analyte in a sample and detecting the interaction between two (or more) proximity probes, when such probes are bound to the analyte. The interaction between the probes (or more specifically, between their respective nucleic acid (or other functional) domains (e.g. an interaction between a nucleic acid domain and an enzyme domain) is thus proximity-dependent; the binding of the proximity probes, together, on the analyte brings them into proximity, such that they (or more particularly, their nucleic acid domains) may interact. Accordingly, by detecting the interaction, for example a ligation reaction (e.g. by detecting a product of the interaction, e.g. the product of the ligation reaction), the analyte may be detected. Thus, in general terms the interaction between the nucleic acid/functional domains of the proximity probes (e.g. between the nucleic acid domains of proximity probes or between a nucleic acid domain and another functional domain on a proximity probe) may lead to the generation of a product, typically a nucleic acid product, which may be detected in order to detect the analyte. Accordingly in step (d) of the method set out above, by detecting said ligation (e.g. by detecting the product of said ligation reaction), the analyte may be detected.

As noted above, proximity-dependent assays based on ligation represent a preferred embodiment of the invention (i.e. wherein at least first and second proximity probes used in the detection method comprise nucleic acid domains and the interaction between them involves a ligation reaction). Viewed generally, the nucleic acid domains of the probes may mediate (e.g. take part in, directly or indirectly, a ligation reaction). Such a ligation reaction may involve ligation of the nucleic acid domains of the proximity probes, and/or the nucleic acid domains may template a ligation reaction.

By way of more specific example, in one embodiment of a method of the invention, the proximity probes may interact by being joined to one another, for example by ligation. The interaction may be detected by detecting the joined product (interaction product; ligation product). In one format of the method the interaction of said nucleic acid domains requires one or more splint oligonucleotides to bind to the domains, and mediate their interaction (specifically in the case of ligation, the splint oligonucleotide which hybridises to the domains and acts as a template for the ligation reaction) and the splint assists in or mediates this interaction. As will be appreciated from the description of various proximity assays above, in other formats/embodiments, the splint may be provided as the nucleic acid domain of a third proximity probe, and/or the ligation of the nucleic acid domains may be direct (i.e. the nucleic acid domains may be ligated directly to one another), or indirect, i.e. they may be ligated indirectly, for example via the intermediacy of a gap oligonucleotide; in one such embodiment the nucleic acid domains may hybridise to the splint oligonucleotide leaving a gap between their respective ends—this gap may be filled by a gap oligonucleotide or by extending the end (a free 3' end) of one of the nucleic acid domains using a polymerase enzyme. Such "gap-fill" embodiments of proximity ligation assays are well-described in the literature, for example in WO 01/61037 or in WO 2007/107743.

In a further specific example, one of more of the nucleic acid domains of the proximity probes may act to template the ligation of one of more added oligonucleotides. In one such embodiment, a first added oligonucleotide may hybridise to both nucleic acid domains, and one or more further oligonucleotides may be added which hybridise to only one of the domains, for example one to each of the nucleic acid domains, each adjacent to each end of the first oligonucleotide, which may be ligated to the first oligonucleotide in a reaction templated by the nucleic acid domains.

In alternative embodiments, the added oligonucleotide(s) may be circularised by the ligation reaction (i.e. akin to a padlock probe as described above). Thus, by way of example the nucleic acid domains of a pair of proximity probes, which are attached to the analyte-specific binding moieties of the respective probes, may have complementarity, respectively, to (i) the 5' and 3' ends, and (ii) region between said ends, of an added linear oligonucleotide (akin to a "padlock probe"). When both probes of the proximity probe pair are brought into proximity due to binding to the same analyte, the nucleic acid domains of the respective probes are able to hybridise to the respective parts of the added oligonucleotide. The nucleic acid domain with complementarity to the 5' and 3' ends of the added oligonucleotide templates the juxtaposed hybridisation, and ligation (on addition of an appropriate ligase), of said ends, resulting in circularisation of the added oligonucleotide. This circularised oligonucleotide is then detected by rolling circle amplification (RCA) using the other nucleic acid domain as a primer; the nucleic acid domain of the other probe of the pair, which is hybridised to a region of the added oligonucleotide between the ligated ends, has a free 3' end. Upon the addition of an appropriate polymerase, the presence of analyte in the sample may be detected by an rolling circle amplification (RCA) of the circularised oligonucleotide. The concatemeric RCA product, which can only be formed when the proximity probes bind in proximity, provides a "surrogate" marker for detection of the analyte.

It will be appreciated that the single added oligonucleotide can be replaced by two oligonucleotides which may be ligated together to form a circle (such a ligation may be templated by one or both nucleic acid domains, but one of the domains will have a free 3' end to act as a primer).

Proximity probing reactions can also be performed by utilizing two free 3' ends, one on each proximity probe with weak complementarity, and when in proximity, a DNA polymerase can extend these ends by adding dNTPs thus forming a detectable DNA template, for example as described in U.S. Pat. Nos. 7,306,904 and 6,511,809. Other hybridisation and extension formats are also possible, for example wherein one nucleic acid domain has a free 3' end and the other a free 5' end, wherein the nucleic acid domains (or more particularly portions of the nucleic acid domains) may hybridise to one another or to a common hybridisation template, or two nucleic acid domains with free 3' ends (or more particularly portions thereof) hybridise to a common hybridisation template, in each case there being at least one free 3' end available following hybridisation, which may be extended to form a detectable extension product. Various examples of proximity extension assays are described in GB1101621.9.

The blocking reagent of, and for use in the method of, the invention comprises in its broadest embodiment a non-analyte-specific binding protein component coupled to a nucleic acid domain.

The non-analyte-specific binding protein component of the blocking reagent can be defined broadly as a protein that has very low or low, i.e. negligible, undetectable or insignificant, or no specific binding affinity for the target analyte of the proximity probe based assay. In other words, it can be seen as the opposite of an analyte-specific binding protein, which can be defined as a protein that is capable of binding specifically, although not necessarily exclusively, to the analyte and will bind preferentially to the analyte in an environment also comprising non-analyte components. Thus a non-analyte-specific binding protein is not capable of binding specifically to the analyte and will not bind preferentially to the analyte in an environment comprising other components. However, the non-analyte-specific binding protein may be capable of binding specifically to other molecules, e.g. non-analytes (which may be molecules that are not present in the proximity probe assay), although it is preferred that the non-analyte-specific binding protein component of the blocking reagent will not have binding affinity specific to any one or more of the components in the proximity probe based assay, i.e. it will be capable of binding only non-specifically, or uniformly, to sites within the assay sample that may otherwise bind the analyte or probe.

Thus the blocking reagent, particularly the protein component of the blocking reagent, must not be capable of specifically binding to the target analyte. Hence, the protein component of the blocking reagent must not bind to the target (e.g. analyte) with greater affinity and/or specificity than to other components in the sample, i.e. any binding to the target analyte may not be distinguished from binding to non-target analytes; the protein component of the blocking reagent either does not bind to target analytes or does so negligibly or non-detectably that any such non-specific binding, if it occurs, may not be distinguished from binding to other non-target analytes. The binding between the blocking reagent and any target or non-target analyte in the sample is typically non-covalent.

In particular, if the protein component of the blocking reagent is able to bind to the target analyte, such binding must be transient and the binding affinity must be less than the binding affinity of the proximity probe for the target analyte. Thus, the binding affinity of protein component of the blocking reagent for the target analyte should be at least an order of magnitude less than the analyte target-binding site of the proximity probe. Preferably, the binding affinity of the protein component of the blocking reagent should be at least 2, 3, 4, 5, or 6 orders of magnitude less than the analyte target-binding site of the proximity probe.

Thus, very low, low or no specific binding affinity for the analyte is where the dissociation constant of the protein component of the blocking reagent for the analyte is at least $10^{-2}$M. By "at least" is meant that the concentration of the protein component of the blocking reagent must be higher to result in 50% of the "binding sites" of the protein component being occupied by the analyte. In the context of the assays of the present invention a $K_d$ in the aforementioned range would result in only a small proportion of the analyte being bound to the blocking reagent. For example, if the blocking reagent was present at a concentration of $10^{-4}$M and the analyte was present at a concentration of $10^{-9}$M and the $K_d$ of the blocking reagent for the analyte was $10^{-2}$M, at any one time the concentration of the blocking reagent:analyte complex could be expected to be $10^{-11}$M, i.e. just 1% of the total analyte would be bound to the blocking reagent. In a preferred embodiment the dissociation constant of the protein component of the blocking reagent for the analyte is at least $10^{-2}$M, $10^{-1}$M, 0.1M, 1M, 2M, 5M or 10M. Thus, no specific binding affinity means that the dissociation constant of the protein component of the blocking reagent is such that at the concentrations used in the proximity probe reactions only non-specific transient interactions would occur between the analyte and the non-analyte-specific binding protein.

Alternatively put, when used in the methods of the invention less than 10% of the analyte will be bound to the protein component of the blocking reagent. More preferably, less than 5%, 4%, 3%, 2% or 1% of the analyte will be bound. Most preferably, less than 0.5%, 0.1%, 0.01% or 0.001% of the analyte will be bound to be protein component of the blocking reagent.

The non-analyte-specific binding protein may be a single species or type of protein, or it may be a mixture of different proteins e.g. different protein types or different species of the same type (the term "species" as used in this context does not have a taxonomical meaning, but rather is intended to denote a protein of a particular specific type). For example where the protein does have a binding specificity to a particular (non-analyte) target, a mixture of proteins of different specificities may be used. It is preferred in such a case that the mixture of proteins does not include a protein having specificity for the target analyte, or alternatively put, that any protein in the mixture does not have specific binding activity for the target analyte or that any binding activity for the target analyte is very low, e.g. negligible or insignificant or undetectable, as defined above.

The non-analyte-specific binding protein component of the blocking reagent is preferably a serum protein or a streptavidin or streptavidin-like protein, or a modification, derivative or variant thereof, or a combination thereof. Where the non-analyte-specific binding protein component of the blocking reagent comprises one or more of the preferred proteins, as defined further below, it will be understood that these proteins are unlikely to have any specific binding affinity for the target analyte.

The serum protein component may be a single specific type of serum protein or may comprise a plurality of proteins of different types and structures. In particular, the serum protein component may be a globulin and/or an albumin protein.

The streptavidin or streptavidin-like protein component may be a single specific type of streptavidin or streptavidin-like protein or a modification, derivative or variant thereof or may comprise a plurality of said proteins. Streptavidin-like proteins can be defined as proteins with similar structural and/or functional properties to streptavidin or modifications, derivatives or variants thereof. For example, avidin, which is found in the whites of eggs from birds, reptiles and amphibians, shows only 30% sequence identity to streptavidin but has an almost identical secondary, tertiary and quaternary structure to steptavidin and is considered to be a streptavidin-like protein. Avidin also shares functional properties with streptavidin in that it is capable of binding biotin with a high degree of affinity or specificity.

Thus, modifications, derivatives or variants of streptavidin or streptavidin-like proteins are also contemplated by the present invention, for example, fragments or truncated proteins, chemically-modified proteins or polypeptides, or variants obtained by genetic engineering, for example polypeptides based on the amino acid sequence of a naturally-occurring streptavidin or avidin proteins, but comprising one or more amino acid substitutions, additions and/or deletions etc. Also included are equivalent or corresponding proteins, which may not necessarily occur naturally but which are structurally or functionally equivalent. Preferably, such modifications include deglycosylated and/or neutral forms of avidin. The streptavidin or streptavidin-like proteins of the invention may be from a single source or multiple sources, i.e. from a single type of organism, e.g. bacterial or animal, or from multiple types of organism, e.g. different strains of bacterium or different species of animal. Synthetically derived or obtained, e.g. recombinant, forms of streptavidin and streptavidin-like proteins are also contemplated. Preferably the streptavidin or streptavidin-like proteins of the invention are selected from the list comprising streptavidin, NeutrAvidin®, Extravidin®, and NeutraLite®. In a particularly preferred embodiment of the invention the protein component of the blocking reagent comprises streptavidin.

Serum protein comprises both globulin and albumin proteins and is derived from blood plasma, and may be defined as the fraction of blood that remains when the cells and platelets have been removed. More specifically, blood serum may be defined as the fraction of blood plasma that does not contain cells, fibrinogen or any other blood clotting factors. Thus, the serum protein may be any protein which may be obtained (or obtainable) from, serum or which may occur in serum. It may be a single protein which may occur in or be obtained from serum, or a mixture of such proteins, or it may be a protein fraction or protein component from serum. The protein component of the blocking reagent of the invention may comprise serum protein in general, that is it may be represented by the serum protein component of serum generally, without separation of a particular protein component. In other words, it may be a mixture of the proteins which occur in serum, and which may be separated therefrom. Thus, the serum protein in the blocking reagent of the invention may comprise both globulin and albumin, and preferably γ-globulin (immunoglobulin) and/or serum albumin. Said serum protein may be from a single blood source or multiple blood sources, i.e. from different animal individuals and/or from different types of animal. Thus serum proteins of or from different species may be used, e.g. from any mammalian species. Although natural sources of serum protein are convenient, a serum protein may be synthetically derived or obtained, for example by recombinant expression, or by derivatisation of a naturally occurring protein. Thus, included within the term "serum protein" are not only any protein which may occur in the serum naturally, but also variants and derivatives thereof, for example, fragments or truncated proteins, chemically-modified proteins or polypeptides, or variants obtained by genetic engineering, for example polypeptides based on the amino acid sequence of a naturally-occurring serum protein, but comprising one of more amino acid substitutions, additions and/or deletions etc. Also included are equivalent or corresponding proteins, which may not necessarily occur in serum but which are structurally or functionally equivalent.

Globulin proteins, pseudoglobulins and euglobulins, are found widely throughout the animal and plant kingdoms and are characterised by their physical properties such as solubility and electrophoretic migration, e.g. pseudoglobulins are soluble in both water and dilute salt solutions, whilst euglobulins are insoluble in water and soluble in dilute salt solutions. Both sub-classes of globulin are coaguable by heat. Any such globulin protein may be used in the present invention. Thus, generally speaking, the blocking reagent of the present invention may comprise any globulin protein. As will be described in more detail below, albumin proteins may also be used, and accordingly the blocking reagent of the invention may comprise any albumin protein.

Prominent sources of globulin proteins are blood plasma and serum, milk, muscle and plant seeds. In particular, the term "globulin" encompasses a heterogeneous group of proteins found in blood serum, which are classified as having a high molecular weight, and both solubility and electrophoretic migration rates lower than for albumin, another class of protein that makes up a major component of blood serum.

Thus, a preferred serum protein for the blocking reagent of the present invention is blood serum globulin, which may comprise four main classes of protein namely: α-1 globulins, α-2 globulins, β-globulins and γ-globulins. However, it will be understood by a person of skill in the art that where serum has been treated to remove fibrinogen and other clotting factors, serum protein comprises only a subset of globulins, predominantly the γ-globulins. The preferred serum protein of the blocking reagent is where the globulin fraction of the serum protein comprises at least 70% γ-globulins, preferably 80% and most preferably at least 90% γ-globulins.

The α-globulins are characterised by their ability to be highly mobile in alkaline or electrically charged solutions and include α-1 antitrypsin and serum amyloid A (α-1 globulins) and haptoglobin and ceruloplasmin (α-2 globulins). β-globulins are characterised by being less mobile in alkaline or electrically charged solutions than α-globulins, but more so than γ-globulins and include plasminogen and transferrin. Thus, γ-globulins are less mobile in alkaline or electrically charged solutions than both the α- and β-globulins and include as the predominant type of protein, the immunoglobulins (antibodies). Antibodies are well described in the art and may be classified in various groups, commonly IgG, IgE, IgD (all monomers), IgA (dimers) and IgM (pentamers).

In a preferred embodiment of invention the protein component of the blocking reagent comprises γ-globulin and particularly immunoglobulin. The preferred class of immunoglobulin of the blocking reagent is IgG. In a particularly preferred embodiment the protein component of the blocking reagent is bulk IgG, i.e. immunoglobulin purified from blood serum comprising a plurality of immunoglobulin (IgG) proteins having a range of binding specificities and affinities. Bulk IgG thus comprises different IgG proteins having different specificities, i.e. a mixture of IgG proteins with different specificities. Preferably the different specificities are non-target analyte-specific binding specificities. Whilst it is contemplated that the protein component of the blocking reagent may comprise an immunoglobulin protein (or albumin protein, as described below) with a specific structure, i.e. binding characteristics, this feature is only practical if the binding properties of that immunoglobulin do not interfere with the detection of the analyte, i.e. the protein component of the blocking reagent must not be capable of binding with specificity and affinity to the analyte, as mentioned above and described in detail below. Preferably therefore the IgG component of the blocking agent, and in particular the bulk IgG, does not have specific binding activity for the target analyte, or any binding to the target analyte which does occur is low, e.g. is insignificant, negligible or undetectable, as defined above. The important point is that any binding of the blocking reagent to the target analyte is not such as to interfere with the performance of the assay. Thus the immunoglobulin component e.g. the IgG or bulk IgG, does not have or has low (or very low) binding activity towards the target analyte.

Of particular interest as the serum protein component of the blocking reagent are antibodies, preferably IgG antibodies, as well as binding fragments and derivatives or mimetics thereof. As such, the protein component of the blocking reagent may be either a monoclonal or polyclonal antibody. In yet other embodiments, the protein component of the blocking reagent is an antibody binding fragment or derivative or mimetic thereof, where these fragments, derivatives and mimetics do not possess the binding affinity for the target analyte. For example, antibody fragments, such as Fv, F(ab)$_2$ and Fab may be prepared by cleavage of the intact protein, e.g. by protease or chemical cleavage. Also of interest are recombinantly or synthetically produced antibody fragments or derivatives, such as single chain antibodies or scFvs, or other antibody derivatives such as chimeric antibodies or CDR-grafted antibodies, where such recombinantly or synthetically produced antibody fragments retain the binding characteristics of the above antibodies, i.e. that they are not capable of binding specifically to the target analyte. Such antibody fragments or derivatives generally include at least the $V_H$ and $V_L$ domains of the subject antibodies, so as to retain the binding characteristics of the subject antibodies. In the case of the protein component of the blocking reagent, the binding characteristics are such that they do not bind to the target analyte. Such antibody fragments, derivatives or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments, derivatives and mimetics thereof may be obtained from commercial sources and/or prepared using any convenient technology, where methods of producing polyclonal antibodies, monoclonal antibodies, fragments, derivatives and mimetics thereof, including recombinant derivatives thereof, are known to those of the skill in the art.

Albumin, as indicated above, forms another major component of blood plasma and serum and proteins in this class are notable for their solubility in water and tendency to coagulate on heat treatment. Thus, in an alternative embodiment the protein component of the blocking reagent may comprise serum albumin protein. It is notable that serum albumin shows significant structural similarity to the immunoglobulins ($\gamma$-globulins). Serum albumin for the blocking reagent of the invention may be derived from a single source, e.g. bovine serum albumin (BSA), human serum albumin (HSA) etc. or may be a combination of different serum albumin proteins.

In a preferred embodiment, where the protein component of the blocking reagent is derived from serum protein as defined above, the serum protein is from the same species as the proteinaceous target analyte binding domain of the proximity probe. Thus, for example, where the analyte binding domain of the proximity probes comprises or is based on an immunoglobulin, e.g. IgG, the protein component of the blocking reagent consists of IgG, preferably bulk IgG, from the same species.

The nucleic acid domain of the blocking reagent may comprise a homogeneous domain, i.e. a single sequence coupled to the protein component of the blocking reagent, or a heterogeneous domain, i.e. a plurality of different sequences with a different sequence being present on the proteins of the protein component of the blocking reagent.

The nucleic acid domain of the blocking reagent is selected on the basis that it will not interfere with the detection of the analyte in the method of the invention. In other words, the nucleic acid domain of the blocking reagent must not have significant sequence identity to the nucleic acid domain of the proximity probes used in the assay. Furthermore, where any other nucleic acid molecules (e.g oligonucleotides) are added to or used in the assay method, for example where one or more splint oligonucleotides and/or gap/cassette oligonucleotides (e.g. as described below) and/or added oligonucleotides for ligation ("ligatable oligonucleotide" or "ligation substrate") and/or blocking oligonucleotides (described below) are used to mediate (or assist) the interaction between the nucleic acid domains of the proximity probes, the nucleic acid domain of the blocking reagent must not have significant sequence identity to those oligonucleotide(s). Furthermore, the nucleic acid domain of the blocking reagent must not hybridise to the analyte or interfere with the method of detecting the interaction of the nucleic acids of the first and second proximity probes, i.e. must not have sequence identity to the primers used in amplification e.g. PCR etc.

Thus, the sequence of the nucleic acid domain of the blocking reagent is not critical as long as it does not hybridise with a nucleic acid domain of a proximity probe used in the assay, or any other oligonucleotide(s) (e.g. splint oligonucleotide and/or ligation substrate (i.e. a ligatable oligonucleotide) added to the reaction mixture, i.e. not present in the original sample) or the analyte, particularly where the target analyte is a nucleic acid. In general, the sequences of the nucleic acid of the blocking reagent should be chosen to avoid the occurrence of hybridization events other than between the nucleic acids that are present in the sample and are not the target analyte of the method. Once the sequence is selected or identified, the nucleic acid domains may be synthesized using any convenient method.

By specifying an absence of significant sequence identity it is meant that the nucleic acid domain of the blocking reagent must have less than 80% sequence identity to the nucleic acid domains of the proximity probes, splints or other oligonucleotides used in the assay, (e.g. oligonucleotides that mediate or assist the interaction between the nucleic acids of the proximity probes) or nucleic acids used in detecting the interaction between the proximity probes. Preferably, the nucleic acid domain of the blocking reagent must have less than 70%, 60%, 50% or less than 40% sequence identity across a substantial part of the nucleic acids in question. In a particularly preferred embodiment of the invention, the nucleic acid domain of the blocking reagent comprises one or more randomly generated nucleic acid sequences. Sequence identity may be determined by any appropriate method known in the art, e.g. the using BLAST alignment algorithm.

Thus, the nucleic acid of the blocking reagent may be a single stranded nucleic acid molecule (e.g. an oligonucleotide), a partially double stranded and partially single stranded molecule, or a double stranded molecule that includes a region that is double stranded and a region where the two nucleic acid strands are not complementary and therefore single stranded. As such, in certain embodiments, the nucleic acid domain is made up of a single stranded nucleic acid. In other embodiments, the nucleic acid domain may be made up of two partially complementary nucleic acid strands, where the two strands include a hybridized region and non-hybridized region.

The nucleic acid domains of the blocking reagent are usually in the range of between about 8 up to about 1000 nucleotides in length, where in certain embodiments they may range from about 8 to about 500 nucleotides in length including from about 8 to about 250 nucleotides in length, e.g., from about 8 to about 160 nucleotides in length, such as from about 12 to about 150 nucleotides in length, from about 14 to about 130 nucleotides in length, from about 16 to about 110 nucleotides in length, from about 8 to about 90 nucleotides in length, from about 12 to about 80 nucleotides in length, from about 14 to about 75 nucleotides in length, from about 16 to about 70 nucleotides in length, from about 16 to about 60 nucleotides in length, and so on. In certain representative embodiments, the nucleic acid domain may range in length from about 10 to about 80 nucleotides in length, from about 12 to about 75 nucleotides in length, from about 14 to about 70 nucleotides in length, from about 34 to about 60 nucleotides in length, and any length between the stated ranges. In some embodiments, the nucleic acid domains are usually not more than about 28, 29, 30, 31, 32, 33, 34, 35, 36, 37, 38, 39, 40, 41, 42, 44, 46, 50, 55, 60, 65, or 70 nucleotides in length.

The nucleic acid domain of the blocking reagent may be made up of ribonucleotides and/or deoxyribonucleotides as well as synthetic nucleotide residues that are capable of participating in Watson-Crick type or analogous base pair interactions. Thus, the nucleic acid domain may be DNA or RNA or any modification thereof e.g. PNA or other derivatives containing non-nucleotide backbones.

Thus, at the extremes the blocking reagent of the invention may comprise a plurality of proteins coupled to a plurality of nucleic acids or a single type of protein, as previously defined, coupled to nucleic acids all consisting of the same sequence, or any combination thereof.

In a particularly preferred embodiment of the invention the blocking reagent comprises bulk IgG coupled to a random oligonucleotide, wherein said oligonucleotide is single stranded DNA. Further preferably, the oligonucleotide is at least 40 nucleotides in length.

The nucleic acid domain is coupled to the protein component of the blocking reagent and this "coupling" or connection may be by any means known in the art, and which may be desired or convenient and may be direct or indirect e.g. via a linking group. For example, the domains may be associated with one another by covalent linkage (e.g. chemical cross-linking) or by non-covalent association e.g., via streptavidin-biotin based coupling (biotin being provided on one domain and streptavidin on the other). In the case where the protein component of the blocking reagent is a streptavidin or streptavidin-like protein or a modification, derivative or variant thereof, the biotin molecule is provided on the oligonucleotide molecule. However, it is contemplated that the streptavidin or streptavidin-like protein or modification, derivative or variant thereof may be coupled to the oligonucleotide of the blocking reagent directly, i.e. by a covalent linkage and in the absence of biotin. As discussed above, it is this aspect of coupling the two components of the blocking reagent that results in the superior effect of blocking reagent in comparison to either component used alone or in combination, where the components are not coupled.

The two components of the blocking reagent are joined together either directly through a bond or indirectly through a linking group. Where linking groups are employed, such groups may be chosen to provide for covalent attachment of the nucleic acid domain and protein component through the linking group. Linking groups of interest may vary widely depending on the nature of the protein component. The linking group, when present, is in many embodiments biologically inert. A variety of linking groups are known to those of skill in the art and find use in the subject blocking reagent. In representative embodiments, the linking group is generally at least about 50 daltons, usually at least about 100 daltons and may be as large as 1000 daltons or larger, for example up to 1000000 daltons if the linking group contains a spacer, but generally will not exceed about 500 daltons and usually will not exceed about 300 daltons. Generally, such linkers will comprise a spacer group terminated at either end with a reactive functionality capable of covalently bonding to the nucleic acid domain or protein component. Spacer groups of interest may include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject blocking reagent include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

In a preferred embodiment of the invention the linker used to couple the non-analyte-specific binding protein component and nucleic acid domain of the blocking reagent is the same as the linker that couples the nucleic acid domain of the proximity probe(s) to the proteinaceous analyte binding domain.

The blocking reagent employed in the subject methods may be prepared using any convenient method. However, in one aspect the present invention also provides a method for producing a blocking reagent comprising:
(a) extracting serum protein from blood;
(b) preparing a nucleic acid; and
(c) coupling the protein of (a) with the nucleic acid of (b).

The serum protein, nucleic acid and coupling may be as defined above. In a preferred aspect of the invention, the serum protein is bulk IgG.

Thus, in a preferred aspect, the present invention provides a blocking reagent comprising bulk IgG coupled to a nucleic acid domain. More generally viewed, this aspect of the present invention can be seen to provide a conjugate comprising bulk IgG coupled to a nucleic acid molecule (or alternatively put, to a nucleic acid domain).

In a further preferred aspect, the present invention provides a blocking reagent comprising an albumin protein coupled to a nucleic acid domain. More generally viewed, this aspect of the present invention can be seen to provide a conjugate comprising an albumin protein coupled to a nucleic acid molecule (or alternatively put, to a nucleic acid domain). Preferably, the albumin protein is a serum albumin protein (e.g. BSA or HSA etc).

In these aspects of the invention, the nucleic acid domain/molecule may be as defined above.

In preferred embodiments (including particularly of the aspects of the invention set out above), the nucleic acid comprises one or more oligonucleotides of random sequence, i.e. a single randomly generated oligonucleotide or a plurality of oligonucleotides each with a different random sequence.

Thus, the invention also provides a blocking reagent obtained or obtainable by the above method and a kit for detecting an analyte in a sample comprising the blocking reagent of the invention. Said kit may further comprise one or more proximity probes, one or more additional oligonucleotides for use in the method (e.g. a splint oligonucleotide, gap oligonucleotide, and/or ligatable oligonucleotide) and means for effecting and/or detecting the interaction of the proximity probes and is defined in detail below.

The term "detecting" is used broadly herein to include any means of determining the presence of the analyte (i.e. if it is present or not) or any form of measurement of the analyte. Thus "detecting" may include determining, measuring, assessing or assaying the presence or absence or amount or location of analyte in any way. Quantitative and qualitative determinations, measurements or assessments are included, including semi-quantitative. Such determinations, measurements or assessments may be relative, for example when two or more different analytes in a sample are being detected, or absolute. As such, the term "quantifying" when used in the context of quantifying a target analyte(s) in a sample can refer to absolute or to relative quantification. Absolute quantification may be accomplished by inclusion of known concentration(s) of one or more control analytes and/or referencing the detected level of the target analyte with known control analytes (e.g., through generation of a standard curve). Alternatively, relative quantification can be accomplished by comparison of detected levels or amounts between two or more different target analytes to provide a relative quantification of each of the two or more different analytes, i.e., relative to each other.

The "analyte" may be any substance (e.g. molecule) or entity it is desired to detect by the method of the invention. The analyte is the "target" of the assay method of the invention. The analyte may accordingly be any biomolecule or chemical compound it may be desired to detect, for example a peptide or protein, or nucleic acid molecule or a small molecule, including organic and inorganic molecules. The analyte may be a cell or a microorganism, including a virus, or a fragment or product thereof. It will be seen therefore that the analyte can be any substance or entity for which a specific binding partner (e.g. an affinity binding partner) can be developed. In the case of proximity probe-based assays all that is required is that the analyte is capable of simultaneously binding at least two binding partners (more particularly, the analyte-binding domains of at least two proximity probes). In the case of other probe-based detection assays, e.g. immuno-PCR, immuno-RCA etc, it is sufficient that the analyte is capable of binding at least one binding partner. Probe-based detection assays, e.g. proximity probe-based assays, such as that of the present invention, have found particular utility in the detection of proteins or polypeptides. Analytes of particular interest may thus include proteinaceous molecules such as peptides, polypeptides, proteins or prions or any molecule which includes a protein or polypeptide component, etc., or fragments thereof. The analyte may be a single molecule or a complex that contains two or more molecular subunits, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA. Of particular interest may be the interactions between proteins and nucleic acids, e.g. regulatory factors, such as transcription factors, and DNA or RNA.

All biological and clinical samples are included, e.g. any cell or tissue sample of an organism, or any body fluid or preparation derived therefrom, as well as samples such as cell cultures, cell preparations, cell lysates etc. Environmental samples, e.g. soil and water samples or food samples are also included. The samples may be freshly prepared or they may be prior-treated in any convenient way e.g. for storage.

Representative samples thus include any material which may contain a biomolecule, or any other desired or target analyte, including for example foods and allied products, clinical and environmental samples. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include whole blood and blood-derived products such as plasma, serum and buffy coat, blood cells, urine, faeces, cerebrospinal fluid or any other body fluids (e.g. respiratory secretions, saliva, milk, etc), tissues, biopsies, cell cultures, cell suspensions, conditioned media or other samples of cell culture constituents, etc. The sample may be pre-treated in any convenient or desired way to prepare for use in the method of the invention, for example by cell lysis or purification, isolation of the analyte, etc.

The probes, e.g. proximity probes, for use in the detection method of the invention comprise a proteinaceous analyte-binding domain and functional domain which is preferably a nucleic acid domain, but as noted above, one or more of the proximity probes used in a proximity assay may comprise a different functional group such as an enzyme. Proximity probes are in effect detection probes which bind to the analyte (via the analyte-binding domain), the binding of which may be detected (to detect the analyte) by means of detecting the interaction which occurs between the functional (e.g. nucleic acid) domains thereof upon such binding. Other probes e.g. immuno-PCR or immuno-RCA probes may function as detection probes, the binding of which to the analyte is detected to detect the presence of analyte. Accordingly, where the functional domain is a nucleic acid molecule, the probes may be viewed as nucleic acid-tagged affinity ligands or binding partners for the analyte, the analyte-binding domain being the affinity binding partner, and the nucleic acid domain the nucleic acid tag. The nucleic acid domain is coupled to the analyte-binding domain and as noted above, this "coupling" or connection may be by any means known in the art, and which may be desired or convenient and may be direct or indirect, e.g. via a linking group. Examples of the way in which a protein may be coupled to a nucleic acid are described in detail above. Preferably, the linker, or the means, used to couple the analyte-binding domain and the nucleic acid domain of the probe (e.g. proximity probe) is same as the linker or means of the blocking reagent.

The analyte-binding domain may be any binding partner for the target analyte, and it may be a direct or indirect binding partner therefor. Thus it may bind to the target analyte directly, or indirectly via an intermediary molecule or binding partner which binds to the target analyte, the analyte-binding domain binding to said intermediary molecule (binding partner). Particularly, the analyte-binding domain or the intermediary binding partner is a specific binding partner for the analyte. A binding partner is any molecule or entity capable of binding to its target, e.g. target analyte, and a specific binding partner is one which is capable of binding specifically to its target (e.g. the target analyte), namely that the binding partner binds to the target (e.g. analyte) with greater affinity and/or specificity than to other components in the sample. Thus binding to the target analyte may be distinguished from non-target analytes; the specific binding partner either does not bind to non-target analytes or does so negligibly or non-detectably or any such non-specific binding, if it occurs, may be distinguished. The binding between the target analyte and its binding partner is typically non-covalent.

The analyte binding domain may be selected to have a high binding affinity for a target analyte. By high binding affinity is meant a binding affinity of at least about $10^{-4}$ M, usually at least about $10^{-6}$ M or higher, e.g., $10^{-9}$ M or higher. The analyte binding domain may be any of a variety of different types of molecules, so long as it exhibits the requisite binding affinity for the target protein when present as part of the proximity probe. In other embodiments, the analyte binding domain may be a ligand that has medium or even low affinity for its target analyte, e.g. less than about $10^{-4}$ M.

In the detection method of the present invention the analyte-binding domain of at least one probe, e.g. proximity probe (but preferably of at least two, or more preferably of all the proximity probes) is a proteinaceous molecule. Thus, the analyte-binding domain may be a small peptide molecule or a larger polypeptide or protein. A peptide may, for example range in size from about 5 to about 100 amino acid residues, usually from about 5 to about 50 residues and more usually from about 10 to about 30 residues. By large polypeptide or protein is meant a molecule ranging in size from about 100 amino acid residues or greater. Of particular interest as analyte-binding domains are antibodies, as well as binding fragments and derivatives or mimetics thereof. Where antibodies are the analyte-binding domain, they may be derived from polyclonal compositions, such that a heterogeneous population of antibodies differing by specificity are each "tagged" with the same tag nucleic acid (nucleic acid domain) or monoclonal compositions, in which a homogeneous population of identical antibodies that have the same specificity for the target analyte are each tagged with the same nucleic acid. As such, the analyte-binding domain may be either a monoclonal or polyclonal antibody. In yet other embodiments, the affinity-binding domain is an antibody fragment or derivative or mimetic thereof, where these fragments, derivatives and mimetics have the requisite binding affinity for the target analyte. Examples of antibodies, antibody fragments, mimetics and derivatives thereof are described above and the present invention contemplates that the affinity-binding domain may be any type of these molecules, provided they have the requisite binding affinity for the target analyte.

Importantly, the analyte-binding domain will be one that includes a moiety that can be covalently attached to the nucleic acid domain without substantially abolishing the binding affinity of the analyte-binding domain to its target analyte.

In one embodiment of the method of the present invention the probes (e.g. proximity probes) may be multivalent (proximity) probes. Such multivalent (proximity) probes comprise at least two, but as many as 100, analyte binding domains conjugated to at least one, and preferably more than one, nucleic acid(s).

The binding sites on the analyte for the respective analyte-binding domains of the proximity probes in a set may be the same or different. Thus, for example in the case of a homomeric protein complex or aggregate comprising two or more identical subunits or protein constituents, the analyte-binding domains of two or more probes may be the same. Where the analyte is a single molecule or comprises different sub-units or constituents (e.g. a heteromeric complex or an aggregate of different proteins), the analyte-binding domains will be different.

Since the length of the nucleic acid domain of the proximity probes can be constructed to span varying molecular distances, binding sites on the analyte for the analyte-binding domain need not be on the same molecule. They may be on separate, but closely positioned, molecules. For example, the multiple binding domains of an organism, such as a bacteria or cell, or a virus, or of a protein complex or interaction can be targeted by the methods of the present invention.

As noted above, the analyte-binding domain may bind to the analyte directly or indirectly. In the case of indirect binding, the target analyte may first be bound by a specific binding partner (or affinity ligand), and the analyte-binding domain of the probe, e.g. proximity probe, may bind to the specific binding partner. This enables the design of probes (e.g. proximity probes) as universal reagents. For example the analyte-specific binding partner may be an antibody, and a universal probe, e.g. proximity probe, set may be used to detect different analytes by binding to the Fc regions of the various different analyte-specific antibodies.

The nucleic acid domains of the probes, e.g. proximity probes, may be regarded as the nucleic acid "tags" which may be detected, or which in the case of proximity probes interact to form a detectable product, which may be detected to report the detection of the analyte. The nucleic acid domains may thus be regarded as reactive nucleic acid functionalities which may provide directly or indirectly or which may interact to provide the signal by means of which the analyte is detected (for example to form a signal-giving product (e.g. they may be ligated together to form a ligation product, or may allow the formation of an extension product, e.g. as detailed above) or to mediate the formation or assist in the formation of a signal-giving product, e.g. as a ligation or extension template and/or primer, for example as an RCA primer). Put another way, the nucleic acid domains may be regarded as "detection tags", which may be detected or which may interact to form a "detectable" tag or product. When two or more analytes are present in the same sample they may be detected simultaneously using two or more probes or sets of proximity probes, each set of proximity probes being designed to form on interaction a unique nucleic acid sequence "detectable tag". These unique "detectable tags" may be detected and quantified (optionally after amplification) separately using methods well known in the literature including liquid chromatography, electrophoresis, mass spectrometry, DNA array technology and multi-colour real-time PCR.

As described above, proximity probe based detection assays are well described in the prior art, e.g. WO 97/00446, WO 01/61037, WO 03/044231, WO 2005/123963 and WO 2007/107743, which are hereby incorporated by reference. Other proximity assays are also known and described in the art, for example in WO 2007/044903 and WO 2009/012220, also incorporated herein by reference. Thus, it is clear that the skilled person would be capable of modifying the detection methods as described herein using methods disclosed in the art, insofar as those methods extend to proximity probe based detection assays that utilise proteinaceous proximity probes. However, particularly preferred aspects of the detections methods of the invention are explained in detail below.

In one preferred method of detection of the present invention, the nucleic acid domains of first and second proximity probes may be joined together, for example by ligation. This "joining" (or "conjugation") may be direct, i.e. the respective nucleic acid domains may be directly joined to one another, or it may be indirect, i.e. the respective nucleic acid domains may be joined indirectly e.g. by joining each to one of the two ends of a further intermediary nucleic acid molecule (e.g. a "gap" oligonucleotide, also known in the art as a "a cassette" oligonucleotide). This "conjugation" or "interaction" (typically ligation) may be mediated by one or more splint oligonucleotides. As such, the splint or gap/cassette oligonucleotide may be added to the sample in the form of an independent nucleic acid, or it may be provided as the nucleic acid domain of a third proximity probe, as explained further below. The interaction (by ligation) results in the formation of a new nucleic acid molecule or sequence, which may be detected.

As mentioned above, and discussed further below, the splint oligonucleotide may hybridise to the nucleic acid domains of the first and second proximity probes, enabling their ligation.

The nucleic acid domains of the proximity probes may be a single stranded nucleic acid molecule (e.g. an oligonucleotide), a partially double stranded and partially single stranded molecule, or a double stranded molecule that includes of a region that is double stranded and a region where the two nucleic acid strands are not complementary and therefore single stranded. As such, in certain embodiments, the nucleic acid domain is made up of a single stranded nucleic acid. In other embodiments, the nucleic acid domain may be made up of two partially complementary nucleic acid strands, where the two strands include a hybridized region and non-hybridized region.

The nucleic acid domains of the proximity probes are generally of a length sufficient to allow splint-mediated interaction with the nucleic acid domain of another proximity probe when bound to a target analyte. Nucleic acid domains are usually in the range of between about 8 up to about 1000 nucleotides in length, where in certain embodiments they may range from about 8 to about 500 nucleotides in length including from about 8 to about 250 nucleotides in length, e.g., from about 8 to about 160 nucleotides in length, such as from about 12 to about 150 nucleotides in length, from about 14 to about 130 nucleotides in length, from about 16 to about 110 nucleotides in length, from about 8 to about 90 nucleotides in length, from about 12 to about 80 nucleotides in length, from about 14 to about 75 nucleotides in length, from about 16 to about 70 nucleotides in length, from about 16 to about 60 nucleotides in length, and so on. In certain representative embodiments, the nucleic acid domain may range in length from about 10 to about 80 nucleotides in length, from about 12 to about 75 nucleotides in length, from about 14 to about 70 nucleotides in length, from about 34 to about 60 nucleotides in length, and any length between the stated ranges. In some embodiments, the nucleic acid domains are usually not more than about 28, 29, 30, 31, 32, 33, 34, 35, 36, 37, 38, 39, 40, 41, 42, 44, 46, 50, 55, 60, 65, or 70 nucleotides in length.

The nucleic acid domain of the proximity probes may be made up of ribonucleotides and/or deoxyribonucleotides as well as synthetic nucleotide residues that are capable of participating in Watson-Crick type or analogous base pair interactions. Thus, the nucleic acid domain may be DNA or RNA or any modification thereof e.g. PNA or other derivatives containing non-nucleotide backbones.

The sequence of the nucleic acid domain of the first and second proximity probes (i.e. the "detection" nucleic acid domains) may be chosen or selected with respect to the splint, which may be provided on a third proximity probe. Thus, the sequence is not critical as long as the first and second domains may hybridise to the third domain (splint). However, the sequences should be chosen to avoid the occurrence of hybridization events other than between the nucleic acid domains of the first and second proximity probes with that of splint(s). For example, the nucleic acids of the proximity probes should not be capable of hybridising to the nucleic acid domain of the blocking reagent or, if present, the gap/cassette oligonucleotide. Once the sequence of the nucleic acid domains is selected or identified, the nucleic acid domains may be synthesized using any convenient method.

The two components of the probe, e.g. proximity probe, are joined together either directly through a bond or indirectly through a linking group. The nucleic acid domains may be coupled to the probe, e.g. proximity probe using methods and linkers as described for coupling the nucleic acid domain and protein component of the blocking reagent, as described above. In a preferred embodiment of the invention, the nucleic acid domains of the probes, e.g. proximity probes, are coupled to the analyte binding domain using the same linker as the blocking reagent.

The probes, e.g. proximity probes and blocking reagent employed in the subject methods may be prepared using any convenient method. In representative embodiments, nucleic acid domains may be conjugated to the analyte-binding domain, either directly or through a linking group. The components can be covalently bonded to one another through functional groups, as is known in the art, where such functional groups may be present on the components or introduced onto the components using one or more steps, e.g. oxidation reactions, reduction reactions, cleavage reactions and the like. Functional groups that may be used in covalently bonding the components together to produce the probe, e.g. proximity probe include: hydroxy, sulfhydryl, amino, and the like. The particular portion of the different components that are modified to provide for covalent linkage may be chosen so as not to substantially adversely interfere with that component's binding affinity for the target analyte. In other words, the covalent linkage should not inhibit the probe, e.g. proximity probe, from binding the target analyte and should not encourage the blocking reagent to bind to the target analyte. Where necessary and/or desired, certain moieties on the components may be protected using blocking groups, as is known in the art, see e.g. Green & Wuts, Protective Groups in Organic Synthesis (John Wiley & Sons) (1991). Methods for producing nucleic acid/antibody conjugates are well known to those of skill in the art. See e.g. U.S. Pat. No. 5,733,523, the disclosure of which is herein incorporated by reference.

In other embodiments, probes, e.g. proximity probes, and the blocking reagent may be produced using in vitro protocols that yield nucleic acid-protein conjugates, i.e. molecules having nucleic acids, e.g. coding sequences, covalently bonded to a protein, i.e. where the analyte-binding domain or protein component is produced in vitro from vectors which encode the probe, e.g. proximity probe. Examples of such in vitro protocols of interest include: RepA based protocols (see e.g., Fitzgerald, Drug Discov. Today (2000) 5:253-258 and WO 98/37186), ribosome display based protocols (see e.g., Hanes et al., Proc. Natl. Acad. Sci. USA (1997) 94:4937-42; Roberts, Curr Opin Chem Biol (1999) June; 3: 268-73; Schaffitzel et al., J Immunol Methods (1999) Dec. 10; 231: 119-35; and WO 98/54312), etc.

The splint may be viewed as a "connector" oligonucleotide which acts to connect or "hold together" the nucleic acid domains of first and second proximity probes, such they may interact, e.g. may be ligated together.

In particular the splint hybridises with the nucleic acid domains of the first and second proximity probes. More particularly, the splint hybridises (anneals) simultaneously with the nucleic acid domains of at least the first and second proximity probes. Where the splint is in the form of a nucleic acid domain of a third proximity probe the hybridisation of the nucleic acid domains of all of the set of proximity probes to each other increases the avidity of the probe-target complex upon binding to the target analyte. This avidity effect contributes to the sensitivity of the assay by supporting the formation of signal-giving proximity probe-target analyte complexes.

The term "hybridisation" or "hybridises" as used herein refers to the formation of a duplex between nucleotide sequences which are sufficiently complementary to form duplexes via Watson-Crick base pairing. Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule. The nucleic acid domains of the first and second proximity probes thus contain a region of complementarity for the splint oligonucleotide, and conversely the nucleic acid domain of the splint oligonucleotide contains regions of complementarity for each of the nucleic acid domains of the first and second proximity probes.

The regions of complementarity (i.e. hybridisation regions) may have a length in the range of 4-30 bp e.g. 6-20, 6-18, 7-15 or 8-12 bp.

The splint nucleic acid domain is generally of a length sufficient to provide for the above described simultaneous binding of nucleic acid domains of the first and second probes. In representative embodiments, the splint oligonucleotides range in length from about 6 to about 500 nucleotides, including from about 20 to about 40 nucleotides, e.g. from about 25 to about 30 nucleotides.

As noted above, in the preferred representative embodiment described above, the interaction between the nucleic acid domains of the first and second proximity probes is a joining of the respective domains. This joining may preferably be a ligation, particularly a template-directed ligation. In such a case, it will clearly be understood that the ligation template will be provided by the splint. Such a ligation may be carried out using a ligase enzyme.

Thus, in a preferred embodiment of the method of the invention, the nucleic acid domains of the first and second probes are ligatable by means of a reaction templated by the hybridised splint, said nucleic acid domains are ligated and the ligation product is detected. In such an embodiment, the splint may therefore be viewed as a "splint template" or "ligation template" or "template oligonucleotide".

For the interaction, or more particularly ligation, to take place, one of the nucleic acid domains of the first and second proximity probes will typically be coupled to the proteinaceous analyte-binding domain by its 5' end (leaving a free 3' hydroxyl end), while the other domain will be coupled via its 3' end (leaving a free 5' phosphate end). One of the first and second proximity probes will thus be a 5' probe having a free 3' hydroxyl group capable of interacting with the 5' phosphate of the other 3' probe.

To be ligatable, the respective first and second nucleic acid domains hybridise to the splint with the 3' end of one lined up to the 5' phosphate of the other. However, as mentioned above and described in more detail below, the ligation of the respective domains need not be direct and they may be ligated together by means of an intermediary oligonucleotide, or whichever of the first or second proximity probe carries a free 3' nucleic acid domain end may be extended using a polymerase to fill the gap until the first and second nucleic acid domains can be joined by a ligation reaction. Thus, the respective 3' and 5' ends need not be hybridised immediately adjacent to one another on the splint (template) but may hybridise to the splint leaving a space (or a stretch of nucleotides) between them.

The hybridisation of the splint simultaneously to both nucleic acid domains of the first and second proximity produces a stable duplexed structure that contains all three nucleic acid domains. Such a duplexed structure brings together the 3' hydroxyl free end of the nucleic acid domain of the first proximity probe and the 5' phosphoryl free end of the nucleic acid domain of the second proximity probe (although as mentioned above, these need not be immediately adjacently juxtaposed).

Thus, the splint may include a first 3' region of complementarity for the nucleic acid domain of the 5' free proximity probe and a second 5' region of complementarity for the nucleic acid domain of the 3' free proximity probe. The first and second regions of the splint may be 3 to 20, 6 to 17, 6 to 15 or 6 to 12 or 8 to 12 nucleotides in length, e.g. about 13 to 17, 12 to 16, 11 to 15, or 12 to 14 nucleotides in length or about 6 to 12, 7 to 11 or 8 to 10 nucleotides in length.

As will be described in more detail below, amplification of the interaction (e.g. ligation) product may be used as part of the detection process. Accordingly, it may in some embodiments be desirable to design the splint so as to minimise any false amplification which may take place in such a step, for example any possibility of the splint acting as a template for the polymerase used in the amplification. Thus for example the splint may be provided as an RNA oligonucleotide or a DNA/RNA hybrid; Taq polymerase typically used in amplification reactions cannot use an RNA template. Alternatively, a similar effect may be achieved using a DNA splint with two short hybridisation regions; since the hybridisation is weak, such a splint will not template DNA polymerisation at the high temperatures used in PCR.

As mentioned above, in one embodiment, the nucleic acid domains of the first and second probes may hybridise to the splint not immediately adjacent to each other, but to leave a gap between them. To enable their conjugation (e.g. ligation) a further oligonucleotide, referred to herein as a "gap" or "cassette" oligonucleotide", may hybridise to the splint in this gap, more particularly to span this gap. Such a gap/cassette oligonucleotide may be hybridised with each of its ends directly adjacent to the end of each of the respective domains, such that each such domain end may be ligated to the gap/cassette oligonucleotide to form a single new nucleic acid product. This requires two ligation events, both of which are templated by the splint. Both the 5' and the 3' end of the gap/cassette oligonucleotide are joined (ligated) to the free end of the nucleic acid domain of the first and second probe, as appropriate. The first and second domains are thus connected, or joined, via the gap/cassette oligonucleotide. Such an arrangement may add flexibility to the nucleic acid domains of the probes. The length of the gap/cassette oligonucleotide (and hence the gap between the ends of the first and second domains when hybridised to the splint) may vary, for example between 4 to 50, e.g. 6-30, 6-25, 6-22, 8-22, 10-22, 6-20, 8-20, 10-20 nucleotides.

The gap/cassette oligonucleotide, which functions as an intermediary oligonucleotide in the ligation of the first and second nucleic acid domains, may be added after the probes have been contacted with the sample. Alternatively, it may be added at the same time or it could be pre-hybridized to the splint oligonucleotide.

The gap may also be filled by extending the nucleic acid domain of whichever of the first or second proximity probe carries a free 3' end, using a polymerase. Once the gap has been filled, the ends are joined by a ligation step.

To carry out the method of the invention, the sample is preferably contacted with the blocking reagent prior to contact with at least one set of probes.

In certain embodiments a sample may be assayed for two or more different target analytes. In such embodiments, the sample is contacted with a set of probes, one for each target analyte, or more preferably a set of proximity probes for each target analyte, such that the number of probes or probe sets contacted with the sample may be two or more, e.g., three or more, four or more etc. Such methods find particular use in multiplex and high-throughput applications.

The amount of proximity probes that is added to a sample may be selected to provide a sufficiently low concentration of proximity probe in the reaction mixture to ensure that the proximity probes will not randomly come into close proximity with one another in the absence of binding to a target analyte, at least not to any great or substantial degree. As such, it is intended that only when the proximity probes bind the analyte through the binding interaction between the analyte-binding domains of the proximity probes and the binding sites of the analyte, do the proximity probes come into close proximity to one another. In representative embodiments, the concentration of the proximity probes in the reaction mixture following combination with the sample ranges from about 1 fM to 1 µM, such as from about 1 pM to about 1 nM, including from about 1 pM to about 100 nM.

Following combination of the sample, blocking reagent and set(s) of probes, e.g. proximity probes, the reaction mixture may be incubated for a period of time sufficient for the probes, e.g. proximity probes, to bind target analyte, if present, in the sample. Preferably the sample is contacted with the blocking reagent before addition of the probes, e.g. proximity probes. In representative embodiments, the blocking reagent and sample may be pre-incubated for a period of time ranging from 5 minutes to about 24 hours prior to the addition of the probes, e.g. proximity probes. Preferably said pre-incubation is from about 20 minutes to 12 hours at a temperature ranging from 4 to about 50° C., preferably at room temperature, e.g. 18-30° C. Following pre-incubation, if such a step is included, the product mixture may be incubated for a period of time ranging from about 5 minutes to about 48 hours, including from about 30 minutes to about 12 hours, at a temperature ranging from about 4 to about 50° C., including from about 20 to about 37° C. Conditions under which the reaction mixture is maintained should be optimized to promote specific binding of the probe, e.g. proximity probe to the analyte, while suppressing unspecific interaction. Conditions should also allow for efficient and specific hybridization between the nucleic acid domains as described above.

In certain embodiments, the effective volume of the incubation mixture is reduced, at least during the portion of the incubation step in which the probes. e.g. proximity probes are binding to target analyte, if present in the sample. In these embodiments, the effective volume of the incubation mixture may be reduced for a number of different reasons. In certain embodiments, the effective volume of the incubation mixture is reduced in order to allow for the use of medium and low affinity analyte-binding domains and/or increase the sensitivity of the assay. For example, in certain embodiments where the effective volume of the incubation mixture is reduced, the analyte-binding domains may be medium or low affinity binders, by which is meant that the analyte-binding domains may have a binding affinity for their target analyte that is less than about $10^{-4}$ M, such as about 1 mM $K_d$. In certain embodiments, the sensitivity of the assay may be increased such that the assay can detect as few as about 100 or fewer target analytes in a 1 µl sample, including as few as about 75 or fewer target analytes in a 1 µl sample, including as few as about 50 or fewer target analytes in a 1 µl sample.

In certain embodiments, a "crowding agent" or "volume excluder" is included in the mixture during the incubation step reviewed above, e.g., to reduce the effective volume of the incubation mixture during binding of the proximity probes to their target analyte. Typically, the "crowding agent" is a water soluble macromolecular material. Suitable macromolecular materials broadly comprise biocompatible natural or synthetic polymers having an average molecular weight of from about 1500 to several million, which do not specifically interact with the other reagents in the mixture, or the product. Such polymers are known in the art as "volume-excluders", as their primary function is to occupy volume in the in vitro reaction medium and provide a highly concentrated environment for biochemical reactions, e.g., approximating in vivo conditions. The volume-excluding polymers must of course be sufficiently soluble to provide the required concentration. Suitable exemplary polymers include, but are not limited to: commercially available polyethylene glycol (PEG) polymers, e.g., having an average molecular weight greater than about 2000, FICOLL polymers such as those having an average molecular weight of about 70,000, bovine plasma albumin, glycogen, polyvinylpyrrolidone, dextran, etc. PEG polymers of higher molecular weights, especially, PEG 1450, PEG 3350, PEG 6000 (also sold as PEG 8000), and PEG 20,000, having average molecular weights of about 1450, 3000-3700, 6000-7500, and 15,000-20,000, respectively, are employed in representative embodiments. PEG 6000 and PEG 8000 are employed in representative embodiments. The concentration of the volume-excluding polymers in the incubation reaction in representative embodiments falls within a range of about 5% w/v to about 45% w/v, depending upon the type of polymer and its molecular weight. In general, it is expected that a given type of polymer of higher molecular weight need be present in lower concentration than the same type of polymer of lower molecular weight to achieve the same effect on enzyme activity.

In those embodiments where a volume excluder is employed, prior to the next step of the method, the incubation mixture may be diluted to account for the presence of the volume excluder, e.g., by at least about 2-fold or more, such as at least about 5-fold or more, including at least about 10-fold or more, depending on the amount of volume excluder that is present, the nature of the dilution fluid, etc., where in representative embodiments the dilution fluid is water or some other suitable aqueous fluid of water and one or more solutes, e.g., salts, buffering agents, etc.

Instead of, or in addition to, the use of a volume excluder, the incubation mixture may be reduced in volume during incubation by removing a portion of the water from the incubation mixture, e.g., via evaporation. In these embodiments, the volume of the fluid may be reduced by at least about 2-fold or more, such as at least about 5-fold or more, including at least about 10-fold or more, as desired. Importantly, not all of the water is removed from the incubation mixture in these embodiments. Any convenient protocol may be employed for reducing the volume of the incubation mixture by removing a select portion of the water therefrom. An instrument for controlling evaporation rate by monitoring and adjusting humidity and temperature may be employed, where in certain embodiments the volume of the incubation mixture is monitored, e.g., by continuously measuring the volume of the incubation mixture, where when appropriately evaporated, the ligation and PCR-mixes may be added, as described above. As desired, a heating block could be used to enhance the evaporation. Alternatively, the volume of the incubation mixture may be reduced by filtrating out water. In representative embodiments, a size exclusion filter is used to selectively contain molecules of sizes larger than a cut off limit while smaller molecules and water is removed by passage through the filter. The force placed on the solution to move it through the filter may be by either centrifugation or vacuum suction.

Upon binding of the binding domains of the proximity probes to the analyte, the nucleic acid domains of the proximity probes come into close proximity to one another. As a result, the splint oligonucleotide, if used, is able to bind (hybridise) to the nucleic acid domain of the first and second probes.

Following the combination of the sample with the blocking reagent and the proximity probes, the gap/cassette oligonucleotide may be added, if used, and allowed to hybridise. The nucleic acid domains of the first and second probes, which may be hybridised to the splint, are then joined together by nucleic acid ligation of the free 3' hydroxyl and 5' phosphate ends of the nucleic acid domains of the first and second proximity probes. The reaction mixture is then assayed for the presence of the interaction. Thus, ligation of the first and second nucleic acid domains is detected, generally by detecting the ligation product thereof.

In general, any convenient protocol that is capable of detecting the presence of proximity dependent interactions may be employed. The detection protocol may or may not require a separation step.

In these representative embodiments, ligation of the splint stabilised nucleic acid domains of the first and second proximity probes is achieved by contacting the reaction mixture with a nucleic acid ligating activity, e.g. provided by a suitable nucleic acid ligase, and maintaining the mixture under conditions sufficient for ligation of the nucleic acid domains to occur.

As is known in the art, ligases catalyze the formation of a phosphodiester bond between juxtaposed 3'-hydroxyl and 5'-phosphate termini of two immediately adjacent nucleic acids when they are annealed or hybridized to a third nucleic acid sequence to which they are complementary (i.e. a template). Any convenient ligase may be employed, where representative ligases of interest include, but are not limited to: Temperature sensitive and thermostable ligases. Temperature sensitive ligases include, but are not limited to, bacteriophage T4 DNA ligase, bacteriophage T7 ligase, and E. coli ligase. Thermostable ligases include, but are not limited to, Taq ligase, Tth ligase, and Pfu ligase. Thermostable ligase may be obtained from thermophilic or hyperthermophilic organisms, including but not limited to, pro-karyotic, eukaryotic, or archael organisms. Certain RNA ligases may also be employed in the methods of the invention.

In this ligation step, a suitable ligase and any reagents that are necessary and/or desirable are combined with the reaction mixture and maintained under conditions sufficient for ligation of the hybridized ligation oligonucleotides to occur. Ligation reaction conditions are well known to those of skill in the art. During ligation, the reaction mixture in certain embodiments may be maintained at a temperature ranging from about 4° C. to about 50° C., such as from about 20° C. to about 37° C. for a period of time ranging from about 5 seconds to about 16 hours, such as from about 1 minute to about 1 hour. In yet other embodiments, the reaction mixture may be maintained at a temperature ranging from about 35° C. to about 45° C., such as from about 37° C. to about 42° C., e.g., at or about 38° C., 39° C., 40° C. or 41° C., for a period of time ranging from about 5 seconds to about 16 hours, such as from about 1 minute to about 1 hour, including from about 2 minutes to about 8 hours. In a representative embodiment, the ligation reaction mixture includes 50 mM Tris pH7.5, 10 mM $MgCl_2$, 10 mM DTT, 1 mM ATP, 25 mg/ml BSA, 0.25 units/ml RNase inhibitor, and T4 DNA ligase at 0.125 units/ml. In yet another representative embodiment, 2.125 mM magnesium ion, 0.2 units/ml RNase inhibitor; and 0.125 units/ml DNA ligase are employed.

Following ligation, the ligation products (ligated nucleic acid domains of the first and second probes) are detected as an indication of the presence, or as a measure of the amount and optionally the location, of analyte in the sample. In these embodiments, the ligated product comprises a single stranded nucleic acid molecule (which is the product of the ligation of the two proximal nucleic acid domains of the first and second probes, and any intermediary gap/cassette oligonucleotide, if used) terminating at each end in an analyte binding domain.

The next step of the method following ligation step is to determine the presence of the ligated product in the reaction mixture in order to detect the target analyte in the sample. In other words, the reaction mixture is screened etc. (i.e., assayed, assessed, evaluated, tested, etc.) for the presence of any resultant ligation products in order to detect the presence of the target analyte in the sample being assayed.

As noted above, in alternative embodiments of proximity assays the product of interaction of the nucleic acid domains of the proximity probes may be an extension product, e.g. wherein the nucleic acid domain of at least one proximity probe is extended (for example using the other nucleic acid domain as extension template), or wherein the nucleic acid domains of the probes hybridise to a common added oligonucleotide (e.g. an added hybridisation template, which may be pre-hybridised to one of the nucleic acid domains) and at least one of the nucleic acid domains and/or the added oligonucleotide may be extended, using the added oligonucleotide or nucleic acid domain respectively as extension template. Such extension products may be detected analogously to the detection of ligation products, as described herein.

The interaction product e.g. ligated product or extension product produced by the above-described methods may, in the broadest sense, be detected using any convenient protocol. The particular detection protocol may vary depending on the sensitivity desired and the application in which the method is being practiced. In certain embodiments, the nucleic acid ligation or extension product may be directly detected without any amplification, while in other embodiments the detection protocol may include an amplification component, in which the copy number of the ligated or extended product nucleic acid is increased, e.g., to enhance sensitivity of the particular assay. Where detection without amplification is practicable, the nucleic acid ligation or extension product may be detected in a number of different ways. For example, one or more of the nucleic acid domains of the proximity probes may be directly labelled, e.g., fluorescently, or otherwise spectrophotometrically, or radioisotopically labelled or with any signal-giving label, such that the ligation product is directly labelled. In these embodiments, the directly labelled ligation product may be size separated from the remainder of the reaction mixture, including unligated directly labelled ligation oligonucleotides (i.e. nucleic acid domain oligonucleotides or cassette oligonucleotides), in order to detect the ligated nucleic acid. Alternatively, conformationally selective probes, e.g., molecular beacons (as described in greater detail below) may be employed to detect to the presence of the ligation product, where these probes are directed to a sequence that spans the ligated nucleic acids and therefore only exists in its entirety in the ligation product. Extension products may be detected similarly, for example using probes designed to bind to the extended product or by incorporation of labelled nucleotides etc.

As indicated above, in certain embodiments of the subject methods, the detection step includes an amplification step, where the copy number of ligated or or extended nucleic acids is increased, e.g., in order to enhance sensitivity of the assay. The amplification may be linear or exponential, as desired, where representative amplification protocols of interest include, but are not limited to: polymerase chain reaction (PCR); isothermal amplification, etc.

Where the detection step includes an amplification step (more specifically a step of in vitro amplification of the conjugated product), the amplified product (or amplification product) may be detected, to detect the analyte.

The polymerase chain reaction (PCR) is well known in the art, being described in U.S. Pat. Nos. 4,683,202; 4,683,195; 4,800,159; 4,965,188 and 5,512,462, the disclosures of which are herein incorporated by reference. In representative PCR amplification reactions, the reaction mixture that includes the above ligated nucleic acids or ligation product, or extension product (which may also be viewed as a template nucleic acid in an amplification reaction) is combined with one or more primers that are employed in the primer extension reaction, e.g., the PCR primers (such as forward and reverse primers employed in geometric (or exponential) amplification or a single primer employed in a linear amplification). The oligonucleotide primers with which the template nucleic acid (hereinafter referred to as template DNA for convenience) is contacted will be of sufficient length to provide for hybridization to complementary template DNA under annealing conditions (described in greater detail below). The primers will generally be at least 10 bp in length, usually at least 15 bp in length and more usually at least 16 bp in length and may be as long as 30 bp in length or longer, where the length of the primers will generally range from 18 to 50 bp in length, usually from about 20 to 35 bp in length. The template DNA may be contacted with a single primer or a set of two primers (forward and reverse primers), depending on whether primer extension, linear or exponential amplification of the template DNA is desired.

In addition to the above components, the reaction mixture produced in the subject methods typically includes a polymerase and deoxyribonucleoside triphosphates (dNTPs).

The desired polymerase activity may be provided by one or more distinct polymerase enzymes. In many embodiments, the reaction mixture includes at least a Family A polymerase, where representative Family A polymerases of interest include, but are not limited to: *Thermus aquaticus* polymerases, including the naturally occurring polymerase (Taq) and derivatives and homologues thereof, such as Klentaq (as described in Barnes et al, Proc. Natl. Acad. Sci. USA (1994) 91:2216-2220); *Thermus thermophilus* polymerases, including the naturally occurring polymerase (Tth) and derivatives and homologues thereof, and the like. In certain embodiments where the amplification reaction that is carried out is a high fidelity reaction, the reaction mixture may further include a polymerase enzyme having 3'-5' exonuclease activity, e.g., as may be provided by a Family B polymerase, where Family B polymerases of interest include, but are not limited to: *Thermococcus litoralis* DNA polymerase (Vent) as described in Perler et al., Proc. Natl. Acad. Sci. USA (1992) 89:5577-5581; *Pyrococcus* species GB-D (Deep Vent); *Pyrococcus furiosus* DNA polymerase (Pfu) as described in Lundberg et al., Gene (1991) 108:1-6, *Pyrococcus woesei* (Pwo) and the like. Where the reaction mixture includes both a Family A and Family B polymerase, the Family A polymerase may be present in the reaction mixture in an amount greater than the Family B polymerase, where the difference in activity will usually be at least 10-fold, and more usually at least about 100-fold. Usually the reaction mixture will include four different types of dNTPs corresponding to the four naturally occurring bases present, i.e. dATP, dTTP, dCTP and dGTP. In the subject methods, each dNTP will typically be present in an amount ranging from about 10 to 5000 μM, usually from about 20 to 1000 μM.

The reaction mixture prepared in this detection step of the subject methods may further include an aqueous buffer medium that includes a source of monovalent ions, a source of divalent cations and a buffering agent. Any convenient source of monovalent ions, such as KCl, K-acetate, NH$_4$-acetate, K-glutamate, NH$_4$Cl, ammonium sulphate, and the like may be employed. The divalent cation may be magnesium, manganese, zinc and the like, where the cation will typically be magnesium. Any convenient source of magnesium cation may be employed, including MgCl$_2$, Mg-acetate, and the like. The amount of Mg$^{2+}$ present in the buffer may range from 0.5 to 10 mM, but will preferably range from about 3 to 6 mM, and will ideally be at about 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

In preparing the reaction mixture of this step of the subject methods, the various constituent components may be combined in any convenient order. For example, the buffer may be combined with primer, polymerase and then template DNA, or all of the various constituent components may be combined at the same time to produce the reaction mixture.

The amplified products of the amplification reaction may be detected using any convenient protocol, where the particular protocol employed may detect the amplification products non-specifically or specifically, as described in greater detail below. Representative non-specific detection protocols of interest include protocols that employ signal producing systems that selectively detect double stranded DNA products, e.g., via intercalation. Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo- or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR, SYTO, SYTOX, PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

In yet other embodiments, a signal producing system that is specific for the amplification product, as opposed to double stranded molecules in general, may be employed to detect the amplification. In these embodiments, the signal producing system may include a probe nucleic acid that specifically binds to a sequence found in the amplification product, where the probe nucleic acid may be labelled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labelled probe nucleic acids include, but are not limited to: fluorescein, the cyanine dyes, such as Cy3, Cy5, Alexa 555, Bodipy 630/650, and the like. Other labels, such as those described above, may also be employed as are known in the art.

In certain embodiments, the specifically labelled probe nucleic acids are labelled with "energy transfer" labels. As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena. As used herein, "energy transfer pair" refers to any two molecules that participate in energy transfer. Typically, one of the molecules acts as a fluorescent group, and the other acts as a fluorescence-modifying group. "Energy transfer pair" is used to refer to a group of molecules that form a single complex within which energy transfer occurs. Such complexes may comprise, for example, two fluorescent groups which may be different from one another and one quenching group, two quenching groups and one fluorescent group, or multiple fluorescent groups and multiple quenching groups. In cases where there are multiple fluorescent groups and/or multiple quenching groups, the individual groups may be different from one another. As used herein, "fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength, or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group, or can do so only poorly. As used herein "direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each others' electronic structure. If the fluorescence-modifying group is a quenching group, this will result in the quenching group preventing the fluorescent group from even emitting light.

The energy transfer labelled probe nucleic acid, e.g., oligonucleotide, may be structured in a variety of different ways, so long as it includes a donor, acceptor and target nucleic acid binding domains. As such, the energy transfer labelled oligonucleotides employed in these embodiments of the method are nucleic acid detectors that include a fluorophore domain where the fluorescent energy donor, i.e., donor, is positioned and an acceptor domain where the fluorescent energy acceptor, i.e., acceptor, is positioned. As mentioned above, the donor domain includes the donor fluorophore. The donor fluorophore may be positioned anywhere in the nucleic acid detector, but is typically present at the 5' terminus of the detector. The acceptor domain includes the fluorescence energy acceptor. The acceptor may be positioned anywhere in the acceptor domain, but is typically present at the 3' terminus of the nucleic acid detector or probe.

In addition to the fluorophore and acceptor domains, the energy transfer labelled probe oligonucleotides also include a target nucleic acid binding domain, which binds to a target nucleic acid sequence found in the amplification product of interest (as described above), e.g., under stringent hybridization conditions (as defined above). This target binding domain typically ranges in length from about 10 to about 60 nucleotides, usually from about 15 to about 30 nt. Depending on the nature of the oligonucleotide and the assay itself, the target binding domain may hybridize to a region of the template nucleic acid or a region of the primer extension product. For example, where the assay is a 5' nuclease assay, e.g., in which a TaqMan® type oligonucleotide probe is employed, the target binding domain hybridizes under stringent conditions to a target binding site of the template nucleic acid, which is downstream or 3' of the primer binding site. In alternative embodiments, e.g., in molecular beacon type assays, the target binding domain hybridizes to a domain of a primer extension product. The overall length of the energy transfer labelled oligonucleotides employed in these embodiments, which includes all three domains mentioned above, typically ranges from about 10 to about 60 nucleotides, usually from about 15 to about 30 nucleotides.

In certain embodiments, the energy transfer labelled oligonucleotide is structured such that energy transfer occurs between the fluorophore and acceptor of the energy transfer labelled oligonucleotide probe upon fluorophore excitation when the energy transfer labelled oligonucleotide is not hybridized to target nucleic acid.

In certain embodiments, the oligonucleotide is a single stranded molecule that does not form intramolecular structures and in which energy transfer occurs because the spacing of the donor and acceptor provides for energy transfer in the single stranded linear format. In these embodiments, energy transfer also occurs between the fluorophore and acceptor of labelled oligonucleotide probe upon fluorophore excitation when the labelled oligonucleotide probe is hybridized to a target nucleic acid. Specific examples of such labelled oligonucleotide probes include the TaqMan® type probes, as described in U.S. Pat. No. 6,248,526, the disclosure of which is herein incorporated by reference (as well as Held et al., Genome Res. (1996) 6:986-994; Holland et al., Proc. Natl. Acad. Sci. USA (1991) 88:7276-7280; and Lee et al., Nuc. Acids Res. (1993) 21:3761-3766). In many of these embodiments, the target nucleic acid binding domain is one that hybridizes to, i.e. is complementary to, a sequence of the template nucleic acid, i.e. the target nucleic acid of the target nucleic acid binding domain is a sequence present in the template nucleic acid (i.e., the pseudotarget or surrogate nucleic acid).

In other embodiments, the probe oligonucleotides are structured such that energy transfer does not occur between the fluorophore and acceptor of the energy transfer labelled oligonucleotide probe upon fluorophore excitation when the energy transfer labelled oligonucleotide probe is hybridized to a target nucleic acid. Examples of these types of probe structures include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes (as described in WO 2000/75378, the disclosure of which is herein incorporated by reference). In many of these embodiments, the target binding sequence or domain comprises a hybridization domain complementary to a sequence of the primer extension product of the amplification reaction, and not to a sequence found in the pseudotarget nucleic acid.

The next step in the subject methods is signal detection from the labelled amplification products of interest, where signal detection may vary depending on the particular signal producing system employed. In certain embodiments, merely the presence or absence of detectable signal, e.g., fluorescence, is determined and used in the subject assays, e.g., to determine or identify the presence or absence of the target nucleic acid via detection of the pseudotarget nucleic acid and/or amplification products thereof. Depending on the particular label employed, detection of a signal may indicate the presence or absence of the target nucleic acid.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter. Fluorescence is suitably monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time.

Where the detection protocol is a real time protocol, e.g., as employed in real time PCR reaction protocols, data may be collected in this way at frequent intervals, for example once every 3 minutes, throughout the reaction. By monitoring the fluorescence of the reactive molecule from the sample during each cycle, the progress of the amplification reaction can be monitored in various ways. For example, the data provided by melting peaks can be analyzed, for example by calculating the area under the melting peaks and these data plotted against the number of cycles.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other. The differential of signal intensities and/or ratios will allow changes in labelled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring).

The data generated as described above can be interpreted in various ways. In its simplest form, an increase or decrease in fluorescence from the sample in the course of or at the end of the amplification reaction is indicative of an increase in the amount of the target analyte present in the sample, e.g., as correlated to the amount of amplification product detected in the reaction mixture, suggestive of the fact that the amplification reaction has proceeded and therefore the target analyte was in fact present in the initial sample. Quantification is also possible by monitoring the amplification reaction throughout the amplification process. Quantification may also include assaying for one or more nucleic acid controls in the reaction mixture, as described above.

In this manner, a reaction mixture may readily be screened (or assessed or assayed etc.) for the presence of target analyte(s). The methods are suitable for detection of a single target analyte as well as multiplex analyses, in which two or more different target analytes are assayed in the sample. In these latter multiplex situations, the number of different sets of probes that may be employed typically ranges from about 2 to about 20 or higher, e.g., as up to 100 or higher, 1000 or higher, etc.

The analysis of many analytes simultaneously and in a single reaction using several different proximity probe sets (multiplexing) is enhanced by the increased specificity and sensitivity obtained when using the blocking reagent of the invention and may be further enhanced with the binding splint method. Each probe set can be designed to produce a unique interaction (e.g. ligation) product that can be used to determine the presence or absence, quantity and/or location of the analytes being interrogated by the probe set. The interaction product may be detected directly or after amplification using any of the well established methods for analysis of nucleic acid molecules known from the literature including liquid chromatography, electrophoresis, mass spectrometry, microscopy, real-time PCR, fluorescent probes etc. Of particular interest is the combination of the binding splint method with a "DNA array" read-out format. Several unique interaction products from a multiplexed proximity assay may be hybridized to a standardized DNA array carrying a number of oligonucleotide sequences (tags) complementary to the ligation product sequences. Each interaction product hybridized to the array may be identified by its location on the DNA array and the detected intensity in a given hybridization spot will be indicative of the quantity of that specific interaction product and hence also of the analyte giving rise to that interaction product. Detection of the interaction products may be accomplished by spectrometry, fluorescence, radioisotopes etc. Fluorescent moieties may conveniently be introduced into the interaction products using fluorescently labelled primers or fluorescently labelled nucleotides in the amplification reaction (PCR). The DNA array may be a simple dot-blot array on a membrane containing a small number of spots or a high density array carrying hundreds of thousands of spots.

The detection step of the method of the invention may be modified in order to further reduce the background associated with non-specific nucleic acid hybridization events. Such modifications include adjustments to the method that will reduce any non-specific nucleic acid hybridization events. In some embodiments, a protein may be added to the mixture containing the sample and the proximity probes in order to reduce weak and non-specific DNA hybridization events. For example, E. coli single strand DNA binding protein has been used to increase the yield and specificity of primer extension reactions and PCR reactions. (U.S. Pat. Nos. 5,449,603 and 5,534,407). The gene 32 protein (single strand DNA binding protein) of phage T4 apparently improves the ability to amplify larger DNA fragments (Schwartz, et al., Nucl. Acids Res. 18: 1079 (1990)) and enhances DNA polymerase fidelity (Huang, DNA Cell. Biol. 15: 589-594 (1996)). When employed, such a protein will be used to achieve a concentration in the reaction mixture that ranges from about 0.01 ng/µL to about 1 µg/µL; such as from about 0.1 ng/µL to about 100 ng/µL; including from about 1 ng/µL to about 10 ng/µL.

In other embodiments, double stranded nucleic acid may be used as the nucleic acid domain of the first and second proximity probes in order to reduce weak and non-specific DNA hybridization events.

As explained above, the method of the invention is designed such that interaction between the nucleic acid domains of the first and second probes (e.g ligation) should occur only if the proximity probes are bound to the analyte. However, as is the case with all assays of this type, this cannot always be guaranteed and there may be some background interaction, e.g. ligation of the nucleic acid domains, if the probes come into proximity randomly in solution (the possibility of this is reduced by requiring the nucleic acid domains of all the probes to hybridise to one another by means of the splint, in order for such interaction to occur). Thus, to further reduce or minimise the possibility of background due to unreacted (i.e. unbound) probes, blocking oligonucleotides may be used in addition to the blocking reagent as described above.

The blocking oligonucleotides bind (i.e. hybridise or anneal) to the free ends of the nucleic acid domains of the first and second proximity probes. Thus a blocking oligonucleotide may bind to the free 3' OH end of the nucleic acid domain of a 5' proximity probe and to the free 5' phosphate end of the nucleic acid domain of a 3' proximity probe. The binding of the blocking oligonucleotide may be out-competed in the presence of a high local concentration of the splint, such as occurs when all the probes are bound together on the analyte. In this way the blocking oligonucleotide may prevent the first and second domains from hybridising to the splint in the absence of analyte binding. Thus the free ends of the 5' and 3' probes may be prevented from interaction in the absence of binding to the analyte. When all the probes are bound to the analyte, the local concentration of the splint, especially when the splint forms the nucleic acid domain of a third proximity probe, is sufficient to out-compete the blocking oligonucleotides; the first and second domains hybridise to the splint and the blocking oligonucleotides are replaced.

The blocking oligonucleotides thus allow a competition-based strategy to be used to reduce background and thus further increase sensitivity of the assay.

The blocking oligonucleotides may range in length from about 4-100 nucleotides, e.g. 6-75 or 10-50. They may hybridise to a region at or near the free end of the nucleic acid domain of the first or second probe ("near" meaning within 1-20 or 1-10, e.g. 1-6 nucleotides of the free 3' or 5' end). The region of hybridisation may be 3-15 nucleotides long e.g. 3-12, 3-10, 3-8, 4-8, 3-6, 4-6.

The blocking oligonucleotides may conveniently be designed to have a hairpin structure such that the blocking oligonucleotide may be ligated to the end of proximity probes which have failed to hybridise to the splint.

The blocking oligonucleotides are typically used in an excess over the respective probes, e.g. an excess of 2-1000 fold, e.g. 20-500, 50-300, 100-500, or 100-300 fold e.g., 20, 200 or 300 fold.

In the case of detecting an analyte with proximity-probes of low affinity and slow binding kinetics, the proximity-probes may be contacted with the sample and incubated at a sufficiently high concentration to promote binding of the proximity probes to the analyte. This incubation step may be quickly diluted in a large volume of cold buffer (e.g., buffer that does not include the analyte or the proximity probes), and a portion of this dilution subsequently added to a ligation reaction mixture. This ligation reaction mixture may contain the cassette oligonucleotide (if used), ATP and ligase enzyme. The low temperature, e.g., ranging from about 0° C. to about 20° C., including from about 4° C. to about 10° C., minimizes the dissociation of existing proximity-probe-analyte complexes while the vast dilution results in a decrease of the concentration of the unbound proximity-probes, thereby lowering their reactivity and minimizing the background signal.

In such embodiments, the assay is performed by using a small incubation volume of from about 1 μl to about 20 μl, such as about 1 μl, or about 2 μl, or about 3 μl, or about 4 μl, or about 5 μl or about 6 μl, of sample, blocking reagent and proximity probes and then adding the cassette in a larger incubation volume of from about 8 μl to about 1.5 ml or more, such as from about 20 μl to about 1.3 ml, such as from about 50 μl to about 1 ml, such as from about 75 μl to about 800 μl, such as from about 100 μl to about 500 μl, such as from about 200 μl to about 300 μl. The effective concentration of the proximity probes in the final incubation volume is thus diluted, reducing the background while maintaining the signal since the binding between the probes and analyte does not have time to dissociate before the first and the second nucleic acid domains are ligated, or hybridised and extended. This approach enables extremely high sensitivity as long as the ligation or extension products can be concentrated from the larger volumes, such as over 100 μl or more, and then detecting the proximity dependent interaction. In such embodiments, the probe-probe interactions can be reduced by using single strand binding proteins.

Problems associated with complex samples may be further addressed by diluting the complex sample prior to the analysis. However, one advantage of the detection method of the present invention is that the blocking reagent effectively reduces the complexity of the sample by occupying potential non-target specific binding sites. Nevertheless, dilution of complex samples may in combination with the blocking reagent of the present invention further reduce the background signal. In essence, the step of diluting the sample will greatly decrease the amount of proteins the probes may bind unspecifically to thereby lowering concentration of probes required. While the analyte will also be diluted, the high sensitivity of the proximity probing will provide good detection and quantification.

The method of the present invention may be employed homogeneously (i.e. in solution) as described above, or alternatively heterogeneously, using a solid phase, for example, in which analyte becomes immobilised on a solid phase, permitting the use of washing steps. The use of solid phase assays offers advantages, particularly for the detection of difficult samples: washing steps can assist in the removal of inhibiting components, and analytes can be enriched from an undesirably large sample volume. Higher concentrations and greater amounts of proximity probes can be used, as unbound analytes and probes can be removed by washing. The ability to remove unbound probes, or probes which have not interacted, by washing also means that the solid phase assay tolerates lower purity proximity probes by comparison with the homogeneous assay.

Immobilisation of the analyte on a solid phase may be achieved in various ways. Accordingly, several embodiments of the solid phase assay, e.g. a solid phase binding splint assay, are contemplated. In one such embodiment, one (or more) of the first or second (or third, if used) proximity probes may be (or may be capable of being) immobilised on a solid phase (or solid support). The analyte can firstly be captured by the one (or more) immobilised (or immobilisable) probes and secondly be bound by subsequently added probe(s). In such a scheme, the previously-mentioned avidity effect may not be present during the binding step but is relevant for the washing steps. Preferably, the sample containing the analyte, is contacted with the blocking reagent prior to contact with the solid phase-bound (i.e. immobilised, or immobilisable) probe(s), preferably at the same time as the non-immobilised/non-immobilisable probe(s) are added to the reaction mixture, such that the avidity effect contributes also to the detection (binding) step.

The immobilised proximity probe may be immobilised, i.e. bound to the support, in any convenient way. Thus the manner or means of immobilisation and the solid support may be selected, according to choice, from any number of immobilisation means and solid supports as are widely known in the art and described in the literature. Thus, the probe may be directly bound to the support, for example via the analyte-binding domain (e.g. chemically crosslinked), it may be bound indirectly by means of a linker group, or by an intermediary binding group(s) (e.g. by means of a biotin-streptavidin interaction). Thus, a proximity probe may be provided with means for immobilisation (e.g. an affinity binding partner, e.g. biotin or a hapten, capable of binding to its binding partner, i.e. a cognate binding partner, e.g. streptavidin or an antibody) provided on the support. The probe may be immobilised before or after binding to the analyte. Further, such an "immobilisable" probe may be contacted with the sample together with the support.

The solid support may be any of the well known supports or matrices which are currently widely used or proposed for immobilisation, separation etc. These may take the form of particles (e.g. beads which may be magnetic or non-magnetic), sheets, gels, filters, membranes, fibres, capillaries, or microtitre strips, tubes, plates or wells etc.

The support may be made of glass, silica, latex or a polymeric material. Suitable are materials presenting a high surface area for binding of the analyte. Such supports may have an irregular surface and may be for example porous or particulate e.g. particles, fibres, webs, sinters or sieves. Particulate materials e.g. beads are useful due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 μm, and have a maximum diameter of preferably not more than 10, and e.g. not more than 6 μm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following the analyte binding steps.

In another embodiment, an immobilised (or immobilisable) analyte-specific probe comprising only a binding domain (i.e. an analyte capture probe) can be used in addition to the non-immobilised proximity probes of the homogeneous binding splint assay. Thus in such an embodiment the analyte is first captured by the immobilised or immobilisable capture probe which serves only to immobilise the analyte on the solid phase, and subsequently the immobilised analyte is incubated with the blocking reagent and the proximity probes. In such an embodiment, the capture probe may be any binding partner capable of binding the analyte, directly or indirectly (e.g. as discussed above in relation to the analyte-binding domain of the proximity probe). More particularly, such a capture probe binds specifically to the analyte. Since this embodiment of the method requires the simultaneous binding of at least three probes (binding domains) to the analyte or analyte complex, potentially at least three different epitopes can be interrogated, conferring high specificity on the assay.

In a further embodiment, the analyte itself may be immobilised (or immobilisable) on the solid phase e.g. by non-specific absorption. In a particular such embodiment, the analyte may be present within cells, being optionally fixed and/or permeabilised, which are (capable of being) attached to a solid support.

The above-described methods result in detection of proximity dependent interactions that are present in the reaction mixture, which in turn provides a measure of the amount of target analyte in the sample being assayed. The measure may be qualitative or quantitative.

It will be apparent that the embodiments described above relate to, but are not limited to, proximity probe ligation assays. Hence, the above features may be applied to other probe-based and proximity-probe based assays, which utilise the blocking reagent described herein.

Accordingly, the above described methods of detecting the presence of one or more target analytes in a complex sample finds use in a variety of different applications.

The subject methods may be used to screen a sample for the presence or absence of one or more target analytes in a sample. As indicated above, the invention provides methods of detecting the presence or quantifying the amount of one or more target analytes in a sample.

The subject methods can be employed to detect the presence of one or more target analytes in a variety of different types of samples, including complex samples having large amounts of non-target entities, where the blocking reagent of the subject methods allows for superior detection of the target analytes(s) over equivalent methods that do not utilise the blocking reagent of the invention. As such, the subject methods are highly sensitive methods of detecting one or more target analytes in a simple or complex sample. The sample that is assayed in the subject methods is, in many embodiments, from a physiological source, as discussed in more detail above.

In addition to detecting a wide variety of analytes, the subject methods may also be used to screen for compounds that modulate the interaction between the analyte binding domain of the proximity probe with the binding region of the analyte i.e. the binding of the analyte-binding domain to the analyte. The term modulating includes both decreasing (e.g., inhibiting) and enhancing the interaction between the two molecules. The screening method may be an in vitro or in vivo format, where both formats are readily developed by those of skill in the art.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents identified in the above screening assays find use in a variety of methods, including methods of modulating the activity of the target analyte, and conditions related to the presence and/or activity thereof.

Also provided are kits that find use in practicing the subject methods, as mentioned above. For example, in some embodiments, kits for practicing the subject methods include the blocking reagent, comprising a non-analyte-specific binding protein coupled to a nucleic acid component as described above. Said kits may further comprise at least one set of proximity probes, wherein at least one proximity probe in a set, but preferably at least two, and more preferably each proximity probe includes a proteinaceous analyte-binding domain and a nucleic acid domain as described above. As indicated above, the certain protocols will employ two or more different sets of such probes for simultaneous detection of two or more target analytes in a sample, e.g., in multiplex and/or high throughput formats. As such, in certain embodiments the kits will include two or more distinct sets of proximity probes. Furthermore, additional reagents that are required or desired in the protocol to be practiced with the kit components may be present, which additional reagents include, but are not limited to one or more of the following: a ligase, gap/cassette oligonucleotide, ligatable oligonucleotides, a polymerase, a common hybridisation template (or "extension template"), blocking oligonucleotides, solid support for immobilisation of probe, binding domain or analyte, means for immobilisation of probe, binding domain or analyte, detection means e.g. fluorescently labelled nucleotides or oligonucleotides, pairs of supplementary nucleic acids, single strand binding proteins, and PCR amplification reagents (e.g., nucleotides, buffers, cations, etc.), and the like. In certain embodiments, the kits may include elements employed in reducing the effective volume of an incubation mixture, as reviewed above, e.g., a volume excluder. The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Accordingly, in a further aspect, the present invention provides a kit for use in a method for detecting an analyte in a sample, said kit comprising:

(a) a blocking reagent comprising a non-analyte-specific binding protein coupled to a nucleic acid; and (b) at least one set of probes, wherein each probe in a set comprises a proteinaceous analyte-binding domain and a nucleic acid domain.

In a particularly preferred embodiment, the present invention provides a kit for use in method for detecting an analyte in a sample, said kit comprising:

(a) a blocking reagent comprising a non-analyte-specific binding protein coupled to a nucleic acid;

(b) at least one set of at least first and second proximity probes, wherein at least one probe in each set, but more preferably wherein each probe, comprises a proteinaceous analyte-binding domain and a nucleic acid domain and wherein each probe in each probe set can simultaneously bind to the analyte;

(c) optionally, means for mediating the interaction between the nucleic acids of said first and second proximity probes (e.g. a splint oligonucleotide and/or a ligase enzyme, or a polymerase enzyme and/or a common hybridisation template); and (d) optionally, means for detecting said interaction.

As indicated above, the means for mediating the interaction between the nucleic acids may include one or more splint oligonucleotides and/or a ligase enzyme, and such means may optionally further comprise other reagents necessary for the ligase reaction. Alternatively, when the assay is a proximity extension assay, the means for mediating the interaction may include a polymerase enzyme and/or a common hybridisation template, and optionally further reagents used in the extension reaction. The means for detecting the interaction, may be any of the means discussed above in the context of the assay methods, e.g. a label provided on the nucleic acid domains of the first and second probe or it may be amplification means and means for detecting amplification products thereof e.g. reagents for a PCR reaction (e.g. amplification primers, and optionally polymerase and/or nucleotides, etc.) and for detecting PCR amplicons etc (e.g. Taqman® probes etc.). In an alternative embodiment, the invention provides a kit for use in a method for detecting an analyte in a sample, said kit comprising:

(a) a blocking reagent comprising a non-analyte-specific binding protein coupled to a nucleic acid;

(b) at least one set of probes, wherein each probe in a set comprises a proteinaceous analyte-binding domain and a nucleic acid domain;

(c) optionally, means for interacting with the nucleic acid domain of said probe to produce a detectable signal (e.g. a circular or circularisable nucleic acid molecule capable of hybridising to the nucleic acid domain of said probe and a ligase and/or polymerase enzyme), preferably wherein said detectable signal is a nucleic acid molecule; and (d) optionally, means for detecting said detectable signal.

The means for interacting between the nucleic acid of said probe to produce a detectable signal may include any nucleic acid molecule capable of interacting specifically with the nucleic acid domain to produce a detectable nucleic acid molecule. For instance, the means may be nucleic acid primers, e.g. a primer pair, and a polymerase enzyme capable of amplifying at least a portion of the nucleic acid domain of the probe in, e.g. a PCR. In a particularly preferred embodiment the means comprise a circular or circularisable nucleic acid molecule (akin to a padlock probe) capable of hybridising to the nucleic acid domain of the probe. The nucleic acid domain may act as the template to ligate the circularisable nucleic acid molecule and/or as the primer for rolling circle amplification (RCA). Thus, the means may also comprise a ligase and/or polymerase enzyme and such means may optionally further comprise other reagents necessary for the ligase and/or polymerase reaction, e.g. a primer for RCA where the nucleic acid domain of the probe does not act as a primer. The means for detecting the interaction, may be any of the means discussed above in the context of the assay methods, e.g. a label provided on the nucleic acid domains of the probe or the interacting nucleic acid(s) or it may be amplification means and means for detecting amplification products thereof e.g. reagents for a PCR reaction (e.g. amplification primers, and optionally polymerase and/or nucleotides, etc.) and for detecting PCR amplicons etc (e.g. Taqman® probes etc.).

The kit may further optionally comprise a gap/cassette oligonucleotide and/or blocking oligonucleotides for the first and, if present, second probes.

The kit may further optionally comprise an immobilised capture probe for the analyte, or a capture probe provided with means for immobilisation. Alternatively, the kit may comprise a solid phase for capture of, or binding to, the analyte, or one or more said first, second or third proximity probes may be immobilised or provided with means for immobilisation.

The invention will be further described with reference to the following non-limiting Examples with reference to the following drawings in which:

FIG. 1 shows the reduction in non-specific background signal in a proximity ligation assay reaction using a mismatched PLA-probe pair (NGF and IL-2) on a human plasma sample and a pure buffer sample. Where "GP" is Goat blocking Probe and "P.D." is Plasma Diluent.

Figure 2:
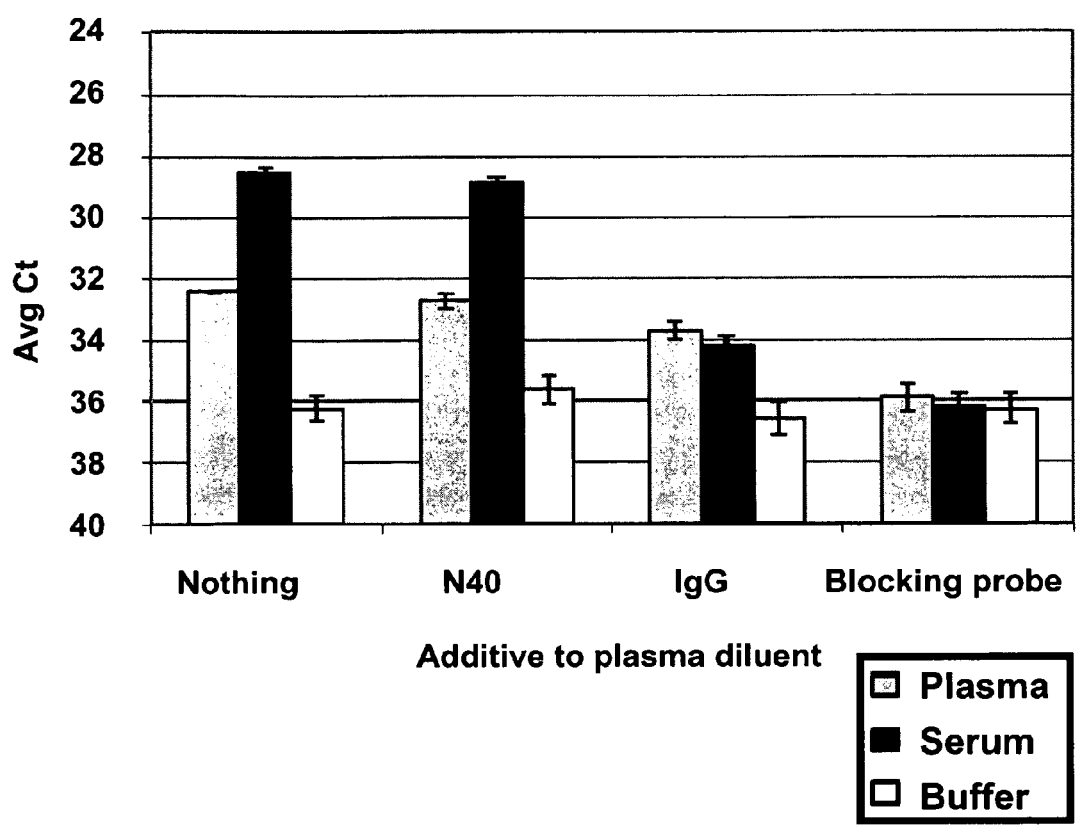

FIG. 2 shows the effect of individual components on the non-specific background signal in a PLA reaction using a mismatched PLA-probe pair (NGF and IL-2) on a human plasma or serum sample, a diluted human plasma or serum sample (50/50) and a pure buffer sample. Where "N40" is a sample of randomised oligonucleotides of 40 nucleotides in length and "IgG" is bulk IgG from goat. The blocking reagent is the N40 oligonucleotides conjugated to the bulk IgG.

Figure 3:
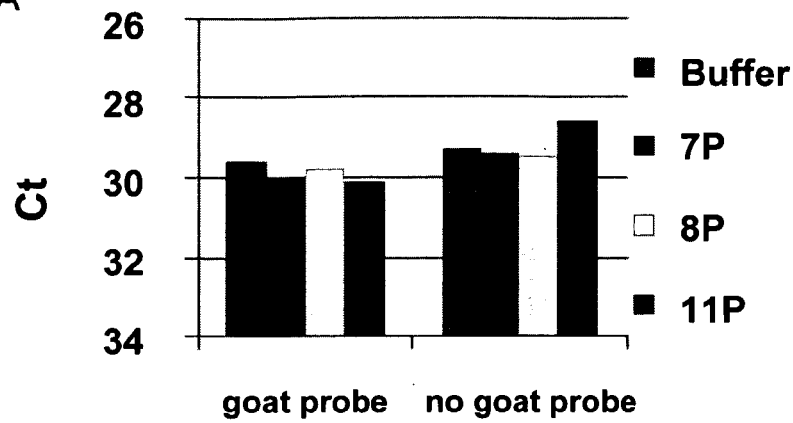
Figure 3:
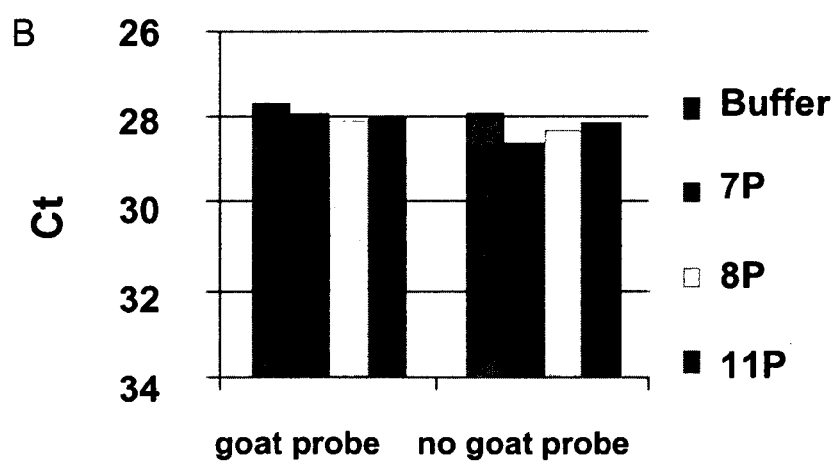
Figure 3:
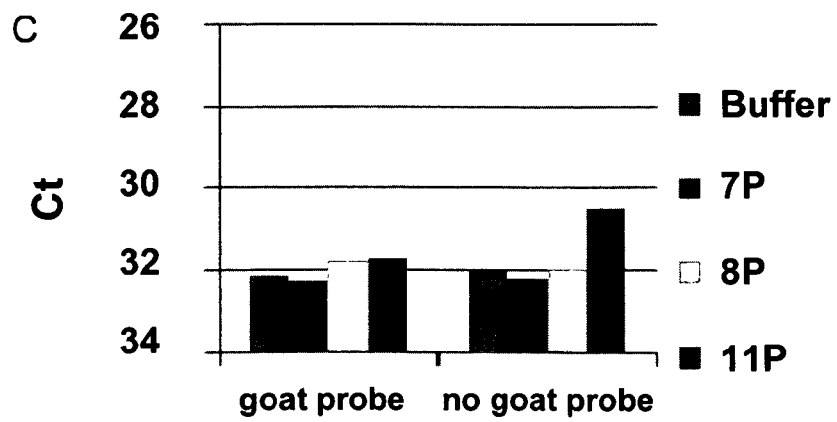

FIG. 3 shows the evaluation of non-specific background signal in a PLA reaction in three human plasma samples, 7P, 8P, 11P, and buffer with and without blocking reagent made from goat (goat probe) and mismatched target-specific antibodies from rabbit and rabbit (A), mouse and rabbit (B) and sheep and mouse (C).

Figure 4:
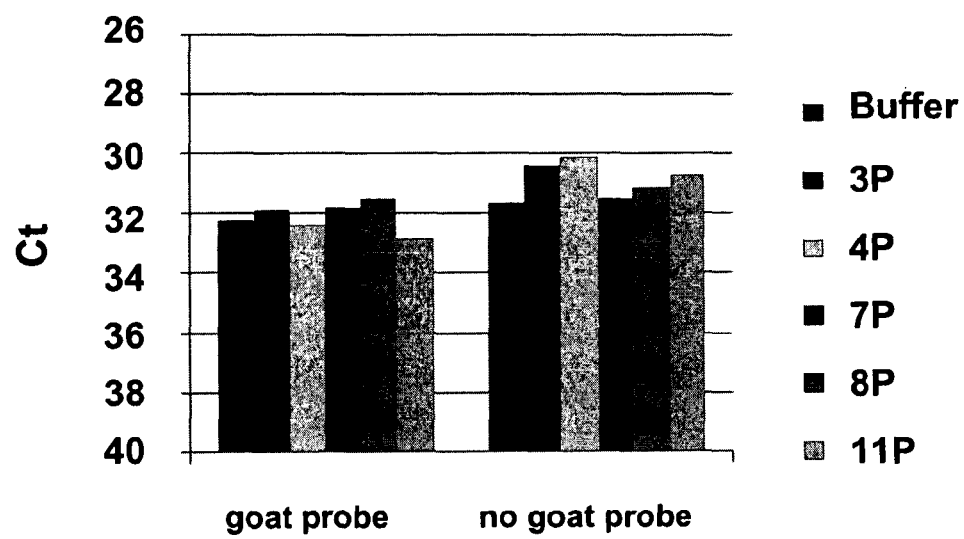
Figure 4:
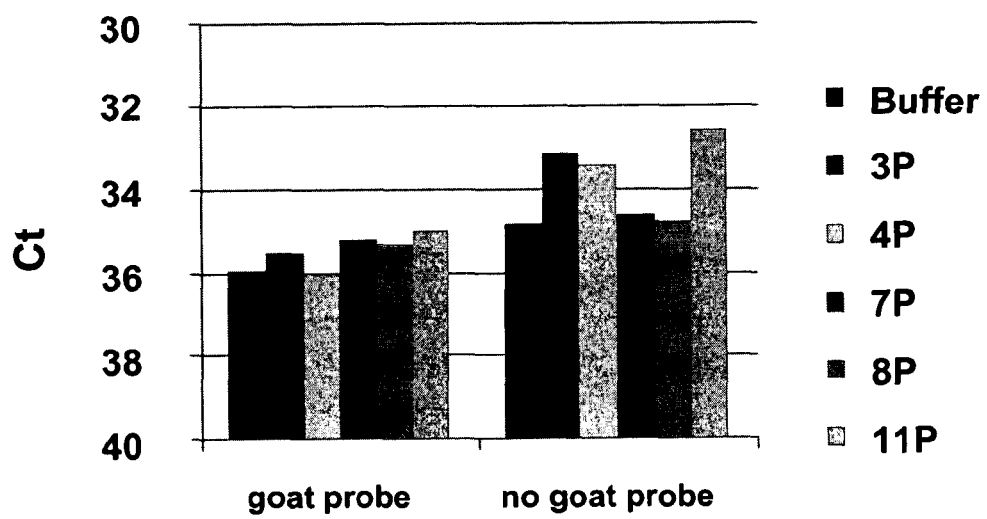

FIG. 4 shows the effect of the blocking reagent (goat probe) in five human plasma samples (3P, 4P, 7P, 8P and 11P) and buffer when using a conjugation chemistry for the target probes ("1-step innova") that is different to the blocking probe ("4-step innova"). The PLA reactions use mismatched probe pairs 51_7 (A) and 7_51 (B) where sequence number 51 corresponds to ICAM and sequence number 7 corresponds to TIMP-1.

EXAMPLE 1

Materials and Methods:

Conjugation of Antibodies

Covalent SMCC Conjugation of Antibodies: For the target-specific probes, polyclonal or monoclonal antibodies were sulfo-SMCC (Sulfosuccinimidyl-4-(N-maleimidomethyl)cyclohexane-1-carboxylate) conjugated to the 3' and 5' oligonucleotides according to the manufacturer's protocol (Pierce Biotechnology, Rockford, Ill., USA). To create the blocking probe, a randomized N40 oligonucleotide was conjugated to a polyclonal IgG antibody made from goat using the same conjugation protocol.

Covalent Innova Conjugation of Antibodies: 10 μg (1 mg/mL) of antibody was conjugated to the 3' and 5' oligonucleotides according to the manufacturer's protocol (Innova Biosciences, Cambridge, United Kingdom). To create the blocking probe, a randomized N40 oligonucleotide was conjugated to a polyclonal IgG antibody made from goat using the same procedure.

Samples

Human EDTA plasma and serum samples were kindly provided by 8 healthy volunteers from Olink Bioscience. K3-EDTA anticoagulant tubes (Hettich Labinstrument, Sollentuna, Sweden) were used for plasma samples and tubes containing a clot activator (Hettich Labinstrument, Sollentuna, Sweden) for serum samples. All samples were incubated for 1-2 hours at RT and were further centrifuged at 3000 rpm for 10 min prior to aliquoting and storage at −20° C.

Sample Preparation

Plasma and serum samples, as well as buffer, were diluted 1:2 in Olink plasma diluent buffer, PBS pH 7.4, 5 mM EDTA, 0.13 mg/mL salmon sperm DNA, 0.1% BSA, 0.25 mg/mL IgG, 0.02% sodium azide, either with or without 2.5 μM of blocking reagent, and incubated for 20 minutes at room temperature.

Probe Incubation

The probe mixes were prepared by diluting the 3' and 5' probes in FBB (PBS pH 7.4, 25 mM Tris pH 8, 0.1% Fish Gelatin, 4 mM EDTA, 1 mM Biotin, 0.016 mg/mL salmon sperm DNA, 0.02% sodium azide), 0.1% Triton X-100/1% BSA to a concentration between 50-200 μM. 2 μL of the probe mix was transferred to each polypropylene cap (Sarstedt, Nümbrecht, Germany), followed by 2 μL of properly diluted sample. The caps were put on the polypropylene tubes, centrifuged shortly and incubated at +4° C. over night.

Ligation and Real-time PCR

100 μL of the ligation mix, containing 25 mM KCl, 2.5 mM MgCl$_2$, 20 mM Tris-HCl (pH 8), 0.004 Weiss units of T4 DNA ligase (Fermentas, St. Leon-Rot, Germany), 100 nM connector oligonucleotide, 2 mM DTT and 80 μM ATP, was added to each 4 μL incubation sample, incubated at 37° C. for 10 minutes and heat-inactivated at 65° C. for 10 minutes. The total reaction volume for real-time PCR was 20 μl, containing 11 μl of 200 nM TaqMan probe, 500 nM universal primers, 1×TE pH 8.0, 2× Fast Taqman Universal Master Mix (Applied Biosystems, Foster City, Calif.) and 9 μl of the ligated product. Samples were run as quadruplicates, and the cycling conditions were 2 min at 95° C., followed by 45 cycles of 15 s at 95° C. and 60 s at 60° C. Amplification and detection were performed using an ABI PRISM 7900 HT (Applied Biosystems, Foster City, Calif.).

Data Analysis

Excel was used for calculations and analysis of the raw data (SDS files) from the q-PCR instrument.

Principle of the Experiments

The following experiments were performed using two PLA probes specific for two different protein analytes that do not interact, such as NGF and IL-2. When a serum or plasma sample is added to such a detection reaction no signal above "buffer" background should be detectable unless there are non-specific binding events by the PLA probes, which bring the probes into proximity, thereby generating false positive signals. The proximity ligation assay converts protein analytes into DNA amplicons which are in the following experiments read by real-time PCR. The average Cts are reported along with the standard deviations.

EXAMPLE 2

Specificity of PLA in the Presence or Absence of the Blocking Reagent

Non-specific signals were monitored experimentally by performing proximity ligation assays in human plasma samples using non-matched probe pairs. Such non-matched or mismatched probe pairs should not give rise to any signal (from plasma) over noise (from pure buffer). The first probe targeted NGF and the other probe targeted IL-2. Plasma signals derived from such a mismatched detection where significantly reduced by the use of the blocking-reagent and including it in the assay procedure (FIG. 1).

Assays were also performed in the presence of non-conjugated bulk IgG and non-conjugated randomized oligonucleotide separately and simultaneously. These reactions did not significantly improve assay specificity, i.e. these to reagents must be conjugated to obtain the reduction in non-specific background signal.

EXAMPLE 3

Assay to Demonstrate that the Specificity Enhancing Effect (Blocking Effect) is Derived from the Specific Blocking Reagent (Antibody Conjugated to Randomized Oligonucleotide) and not from the Individual Components of the Reagent To verify that the blocking effect is obtained only when the randomized N40 oligonucleotide was linked to the bulk IgG antibody, the effects of the individual components were investigated separately and compared to the effect of the blocking reagent. Addition of just the N40 oligonucleotide (7.5 µM during preincubation of plasma or serum, plasma or serum diluent (50:50, plasma or serum and buffer) or buffer alone for 20 min RT did not make any difference on the non-specific signals compared to no additive at all. Addition of the IgG antibody (2.5 µM) reduced the non-specific signals slightly but still there was a significant cross-reactivity in the plasma and serum sample. However, addition of the blocking probe (2.5 µM of antibody with a 3-fold conjugation excess of N40 oligonucleotide) completely eliminated the cross-reactivity (FIG. 2).

EXAMPLE 4

The Blocking Effect of the Blocking Reagent Made from IgG from Species Different to the Species from which the Target-antibodies were Obtained To further evaluate the effect of the blocking reagent we investigated whether the effect of using a probe made of goat IgG could have the same blocking effect on mismatched probes made from other species than goat. We tested three different combinations of mismatched probe pairs; rabbit+rabbit (FIG. 3A), mouse+rabbit (FIG. 3B) and sheep+mouse (FIG. 3C) and studied the cross-reactivity in three different human plasma samples, 7P, 8P and 11P. The only sample to display any cross-reactivity between the mismatched probes was 11P when using the combination rabbit+rabbit (FIG. 3A) and sheep+mouse (FIG. 3C), where no blocking reagent was present in the plasma diluent or buffer. This cross-reactivity illustrates the need for a blocking reagent in order to remove unspecific signals which can appear in certain specific samples. Thus, when the blocking reagent was incubated in the plasma diluents or buffer, the cross-reactivity of the non-specific signals was eliminated. This experiment demonstrates that the protein component of the blocking reagent does not need to originate from the same species as the species from which the target specific analyte binding domain was derived.

EXAMPLE 5

The Blocking Effect of the Blocking Reagent Using One Conjugation Chemistry for the Blocking Reagent and Different Conjugation Chemistry for the Target-specific Probes In the following experiment one linkage type ("4-step Innova") was used for the blocking reagent and another linkage type ("1-step Innova") was used for the target-specific probes. Five different plasma samples were included in the experiment (3P, 4P, 7P, 8P and 11P) and two mismatched probe combinations were used (51_7 and 7_51; sequence number 51 corresponds to an anti-ICAM antibody and sequence number 7 corresponds to TIMP-1). The non-specific binding in the plasma samples was significantly reduced when using the blocking reagent (goat probe) for both combinations of the probes (FIG. 4A-B). Thus, the method and linker used to conjugate/couple the nucleic acid domain of the blocking reagent does not need to be the same as the linker used to conjugate the nucleic acid domain and analyte-binding domain of the proximity probe.

This experiment also demonstrates that whilst only some of the plasma samples showed non-specific signals, all could be removed using the blocking reagent.

The invention claimed is:
1. A kit for use in a method for detecting an analyte in a sample, said kit comprising:
(a) a blocking reagent comprising a non-analyte-specific binding protein conjugated to a nucleic acid domain; and
(b) at least one set of probes, wherein each probe in a set comprises a proteinaceous analyte-specific binding domain and a nucleic acid domain.
2. The kit of claim 1, wherein the at least one set of probes (b) comprises at least one set of at least first and second proximity probes, wherein at least one probe in each proximity probe set comprises a proteinaceous analyte-specific binding domain and a nucleic acid domain, and wherein each probe in each probe set can simultaneously bind to the analyte.
3. The kit of claim 2, wherein said kit further comprises:
(c) means for interacting with the nucleic acid domain of said probe to produce a detectable signal.
4. A method of detecting an analyte in a sample using the kit of claim 1, said method comprising contacting the sample with said blocking reagent (a) and with said at least one set of probes (b), and detecting probes which have bound to the analyte, thereby to detect said analyte.
5. The method of claim 4, wherein the probes are proximity probes comprising a proteinaceous analyte-specific binding partner conjugated to a nucleic acid domain.
6. The method of claim 4, wherein the method of detection is immuno-PCR or immuno-RCA.
7. The method of claim 4, wherein the blocking reagent is added to the sample in an excess over the probes.
8. The method of claim 4, wherein the non-analyte-specific binding protein of the blocking reagent is a serum protein or a streptavidin or streptavidin-like protein, or a modification, derivative or variant thereof, or a combination thereof.
9. The method of claim 8, wherein the non-analyte-specific binding protein is a single specific type of serum protein.
10. The method of claim 8, wherein the non-analyte-specific binding protein is a globulin and/or an albumin protein.
11. The method of claim 10, wherein the non-analyte-specific binding protein is blood serum globulin.
12. The method of claim 11, wherein the blood serum globulin comprises at least 70% γ-globulins.
13. The method of claim 12, wherein the γ-globulins are immunoglobulin.
14. The method of claim 13, wherein the γ-globulin is IgG.
15. The method of claim 14, wherein the IgG is bulk IgG.
16. The method of claim 10, wherein the non-analyte-specific binding protein is serum albumin.
17. The method of claim 16, wherein the serum albumin is a combination of different serum albumin proteins.
18. The method of claim 8, wherein the non-analyte-specific binding protein is from the same species as the proteinaceous target analyte-specific binding domain of the proximity probe.
19. The method of claim 8, wherein the non-analyte-specific binding protein is a streptavidin-like protein with similar structural and/or functional properties to streptavidin or a modification, derivative or variant thereof.
20. The method of claim 8, wherein the non-analyte-specific binding protein is selected from the group consisting of streptavidin, avidin and deglycosylated avidin.
21. The method of claim 4, wherein the nucleic acid domain of the blocking reagent is homogeneous.
22. The method of claim 4, wherein the nucleic acid domain of the blocking reagent is heterogeneous.
23. The method of claim 4, wherein the nucleic acid domain of the blocking reagent:

(i) has less than 80% sequence identity to the nucleic acid domains of the probes, splints or other oligonucleotides used in the method or to any nucleic acid used in detecting interaction between the proximity probes; and/or (ii) comprises one or more randomly generated nucleic acid sequences; and/or (iii) comprises at least 8 nucleotides; and/or (iv) comprises single stranded DNA.

24. The method of claim 4, wherein the non-analyte-specific binding protein is conjugated to the nucleic acid by covalent linkage.

25. The method of claim 24, wherein the covalent linkage is chemical cross-linking.

26. The method of claim 4, wherein the non-analyte-specific binding protein is conjugated to the nucleic acid by non-covalent association.

27. The method of claim 26, wherein the non-covalent association is via streptavidin-biotin based conjugation.

28. The method of claim 4, wherein a linker which conjugates the non-analyte-specific binding protein and nucleic acid domain of the blocking reagent is the same as a linker that conjugates the nucleic acid domain of the probe(s) to the proteinaceous analyte-specific binding domain.

29. The method of claim 5, wherein said method comprises:

(a) contacting said sample with the blocking reagent;

(b) contacting said sample with at least one set of at least first and second proximity probes, which probes each comprise a proteinaceous analyte-specific binding domain and a nucleic acid domain and can simultaneously bind to the analyte;

(c) allowing the nucleic acid domains of the proximity probes to interact with each other upon binding of said proximity probes to said analyte, wherein said interaction comprises a ligation reaction or an extension reaction; and (d) detecting said ligation or extension.

30. The method of claim 4 wherein the sample is contacted with said blocking reagent before being contacted with said probes.

31. The method of claim 4 wherein the sample is contacted with the blocking reagent and probes and incubated.

32. The method of claim 29, wherein the sample is contacted with said blocking reagent before being contacted with said proximity probes.

33. The method of claim 29, wherein the sample is contacted with the blocking reagent and proximity probes and incubated.

34. The method of claim 8, wherein the non-analyte-specific binding protein comprises a plurality of different serum proteins.

35. The kit of claim 2, wherein each probe in each proximity probe set comprises a proteinaceous analyte-specific binding domain and a nucleic acid domain.

36. The kit of claim 2, wherein the kit further comprises (c) means for mediating the interaction between the nucleic acids of said first and second proximity probes.

37. The kit of claim 36, wherein the kit further comprises (d) means for detecting said interaction.

38. The kit of claim 3, wherein said detectable signal is a nucleic acid molecule.

39. The kit of claim 3, wherein said kit further comprises (d) means for detecting said detectable signal.

40. The kit of claim 1, wherein the non-analyte-specific binding protein is bulk IgG.

* * * * *